US006472164B1

United States Patent
Shimokawatoko et al.

(10) Patent No.: US 6,472,164 B1
(45) Date of Patent: Oct. 29, 2002

(54) METHOD FOR EVALUATING THE ABILITY OF A COMPOUND TO INHIBIT THE PROTOPORPHYRINOGEN OXIDASE ACTIVITY

(75) Inventors: Yasutaka Shimokawatoko, Kobe; Shoichi Nishio, Toyonaka, both of (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/289,180

(22) Filed: Apr. 9, 1999

(30) Foreign Application Priority Data

Apr. 10, 1998 (JP) .......................... 10-099619

(51) Int. Cl.[7] .......................... C12Q 1/26; C12N 9/02; C12N 1/20; C12N 15/52; C12N 5/10
(52) U.S. Cl. .................. 435/25; 435/189; 435/325; 435/252.3; 435/320.1; 536/23.2
(58) Field of Search ................ 435/4, 25, 325, 435/252.3, 189, 320.1; 536/23.2

(56) References Cited

U.S. PATENT DOCUMENTS

| 5,767,373 A | 6/1998 | Ward et al. ............... 800/205 |
| 5,939,602 A | 8/1999 | Volrath et al. ............. 800/300 |
| 6,018,105 A | 1/2000 | Johnson et al. ............ 800/298 |
| 6,023,012 A | 2/2000 | Volrath et al. ............. 800/300 |

FOREIGN PATENT DOCUMENTS

| WO | 9704089 | 2/1997 |
| WO | 9829554 | 7/1998 |

OTHER PUBLICATIONS

Koichi Nishimura et al., Gene, vol. 133, 1993, pp. 109–113.
Fumiaki Yamao et al., Jpn. J. Genet., vol. 63, 1988, pp. 237–249.
Kazumasa Miyamoto et al., J. Mol. Biol., vol. 219, 1991, pp. 393–398.
Jean–Michel Camadro et al., Biochemical and Biophysical Research Communications, vol. 106, No. 3, 1982, pp. 724–730.

*Primary Examiner*—Ponnathapu Achutamurthy
*Assistant Examiner*—Delia M. Ramirez
(74) *Attorney, Agent, or Firm*—Birch, Stewart, Kolasch & Birch, LLP

(57) ABSTRACT

The present invention provides a method for evaluating the ability of a compound to inhibit protoporphyrinogen oxidase activity with a host cell deficient in protoporphyrinogen oxidase production which has been transformed with a vector comprising a DNA fragment encoding a protoporphyrinogen oxidase. Transformed cells are grown in protoheme-free medium in the presence and absence of test compounds and growth rates measured under these condition are compared to determine if inhibition has occurred.

6 Claims, 3 Drawing Sheets

SEQUENCE LISTING

<160> NUMBER OF SEQ ID NOS: 14

<210> SEQ ID NO 1
<211> LENGTH: 477
<212> TYPE: PRT
<213> ORGANISM: Rattus norvegicus

<400> SEQUENCE: 1

```
Met Ala Arg Thr Val Ile Val Leu Gly Gly Ile Ser Gly Leu Ala
 1               5                  10                  15

Ala Ser Tyr His Leu Thr Arg Ser Pro Ser Pro Lys Val Ile Leu
                20                  25                  30

Val Glu Gly Ser Lys Arg Leu Gly Gly Trp Ile Arg Ser Val Arg Gly
                35                  40                  45

Ser Asp Gly Ala Ile Phe Glu Leu Gly Pro Arg Gly Ile Arg Pro Ala
     50                  55                  60

Gly Ala Leu Gly Ala Arg Thr Leu Leu Val Ser Glu Leu Gly Leu
 65                  70                  75                  80

Glu Ser Glu Val Leu Pro Val Arg Gly Asp His Pro Ala Ala Gln Asn
                85                  90                  95

Arg Phe Leu Tyr Val Gly Gly Ala Leu His Pro Leu Pro Ser Gly Leu
                100                 105                 110

Arg Gly Leu Leu Arg Pro Ser Pro Phe Ser Lys Pro Leu Phe Trp
                115                 120                 125

Ala Gly Leu Arg Glu Leu Thr Lys Pro Arg Gly Lys Glu Pro Asp Glu
     130                 135                 140

Thr Val His Ser Phe Ala Gln Arg Arg Leu Gly Pro Glu Val Ala Ser
145                 150                 155                 160

Leu Ala Met Asp Ser Leu Cys Arg Gly Val Phe Ala Gly Asn Ser Gln
                165                 170                 175

Glu Leu Ser Ile Arg Ser Cys Phe Pro Ser Leu Phe Gln Ala Glu Gln
                180                 185                 190

Thr His Gly Ser Met Leu Leu Gly Leu Leu Gly Ala Gly Gln Thr
                195                 200                 205

Pro Gln Pro Asn Ser Ser Leu Ile Arg Gln Ala Arg Ala Glu Arg Trp
     210                 215                 220

Ser Gln Trp Ser Leu Arg Gly Gly Leu Glu Met Leu Pro Gln Ala Leu
225                 230                 235                 240

His Asn Tyr Leu Thr Ser Lys Gly Val Thr Ile Leu Ser Gly Gln Pro
                245                 250                 255

Ala Cys Gly Leu Ser Leu Gln Pro Glu Gly His Trp Lys Val Ser Leu
                260                 265                 270

Gly Asp Ser Ser Leu Glu Ala Asp His Ile Ile Ser Thr Ile Pro Ala
                275                 280                 285

Ser Val Leu Ser Lys Leu Leu Pro Ala Glu Ala Pro Leu Ala His
                290                 295                 300

Ile Leu Ser Thr Ile Gln Ala Val Ser Val Ala Val Asn Leu Gln
305                 310                 315                 320

Tyr Lys Gly Ala Cys Leu Pro Val Gln Gly Phe Gly His Leu Val Pro
                325                 330                 335

Ser Ser Glu Asp Pro Thr Val Leu Gly Ile Val Tyr Asp Ser Val Ala
                340                 345                 350

Phe Pro Glu Gln Asp Gly Asn Pro Pro Gly Leu Arg Leu Thr Val Met
```

-continued

```
                 355                 360                 365
Leu Gly Gly Tyr Trp Leu Gln Lys Leu Lys Ala Asn Gly His Glu Leu
    370                 375                 380

Ser Pro Glu Leu Phe Gln Arg Ala Ala Gln Ala Ala Ala Thr Gln
385                 390                 395                 400

Leu Gly Leu Lys Glu Gln Pro Ser His Cys Leu Val His Leu His Lys
                405                 410                 415

Asn Cys Ile Pro Gln Tyr Thr Leu Gly His Trp Gln Lys Leu Asp Ser
                420                 425                 430

Ala Leu Gln Phe Leu Thr Ala Gln Arg Leu Pro Leu Thr Leu Ala Gly
            435                 440                 445

Ala Ser Tyr Glu Gly Val Ala Val Asn Asp Cys Ile Glu Ser Gly Arg
        450                 455                 460

Gln Ala Ala Ile Ala Val Leu Gly Thr Glu Ser Asn Ser
465                 470                 475

<210> SEQ ID NO 2
<211> LENGTH: 1638
<212> TYPE: DNA
<213> ORGANISM: Rattus norvegicus
<220> FEATURE:
<222> LOCATION: (143)...(1576)

<400> SEQUENCE: 2
cgtacacgcg cgttttgcat tagttgctca ttaatcagta agtgcccaga ggtgggtac      60 gggacccgtg gggtttctgc agttgtaaag cagggtgcct cccgttctcc tggggtatct    120
cgactttccc ccaggcctta cg atg gcc cgg act gtg ata gtg ctt ggc gga    172
                          Met Ala Arg Thr Val Ile Val Leu Gly Gly
                           1               5                  10 ggt atc agc gga ttg gcc gca agt tat cat ctg acc cga agc ccc agt     220
Gly Ile Ser Gly Leu Ala Ala Ser Tyr His Leu Thr Arg Ser Pro Ser
                15                  20                  25 cct cct aag gtg atc tta gtg gag ggc agc aaa cgt ttg gga ggc tgg    268
Pro Pro Lys Val Ile Leu Val Glu Gly Ser Lys Arg Leu Gly Gly Trp
            30                  35                  40 atc cgt tca gtc cga gga tca gat ggt gcg atc ttt gaa ctt gga cct    316
Ile Arg Ser Val Arg Gly Ser Asp Gly Ala Ile Phe Glu Leu Gly Pro
        45                  50                  55 cga gga att agg ccg gct gga gcc ctg gga gcc cgg acc ctg ctc ctg    364
Arg Gly Ile Arg Pro Ala Gly Ala Leu Gly Ala Arg Thr Leu Leu Leu
    60                  65                  70 gtt tct gaa ctt ggc ttg gaa tcc gaa gtc ttg cct gtc cga ggg gat    412
Val Ser Glu Leu Gly Leu Glu Ser Glu Val Leu Pro Val Arg Gly Asp
75                  80                  85                  90 cat cca gct gcc cag aac cgg ttc ctg tat gta ggc ggt gcc ctg cac    460
His Pro Ala Ala Gln Asn Arg Phe Leu Tyr Val Gly Gly Ala Leu His
                95                  100                 105 ccc cta ccc tct ggc ctc agg ggg cta ctt cgt cct tca ccc ccc ttc    508
Pro Leu Pro Ser Gly Leu Arg Gly Leu Leu Arg Pro Ser Pro Pro Phe
            110                 115                 120 tca aaa cct cta ttt tgg gct gga ctg agg gag ttg acg aag ccc agg    556
Ser Lys Pro Leu Phe Trp Ala Gly Leu Arg Glu Leu Thr Lys Pro Arg
        125                 130                 135 ggc aaa gag cct gat gag act gtg cac agt ttt gcc cag cgc cgc ctt    604
Gly Lys Glu Pro Asp Glu Thr Val His Ser Phe Ala Gln Arg Arg Leu
    140                 145                 150 gga cct gag gtg gcg tct ctg gct atg gac agc ctt tgc aga gga gtg    652
Gly Pro Glu Val Ala Ser Leu Ala Met Asp Ser Leu Cys Arg Gly Val
```

-continued

```
              155                 160                 165                 170
ttt gct ggc aac agc caa gag ctc agc atc cgg tcc tgc ttt ccc agt       700
Phe Ala Gly Asn Ser Gln Glu Leu Ser Ile Arg Ser Cys Phe Pro Ser
                175                 180                 185 ctc ttc caa gct gaa caa acc cac ggg tcc atg tta ctg ggg ctg ctg       748
Leu Phe Gln Ala Glu Gln Thr His Gly Ser Met Leu Leu Gly Leu Leu
                190                 195                 200 ctg ggg gca ggg caa act cca cag ccc aat tcc tca tta att cgt cag       796
Leu Gly Ala Gly Gln Thr Pro Gln Pro Asn Ser Ser Leu Ile Arg Gln
            205                 210                 215 gcc cgc gct gag cga tgg agt cag tgg tca ctc cgt gga ggg ctg gag       844
Ala Arg Ala Glu Arg Trp Ser Gln Trp Ser Leu Arg Gly Gly Leu Glu
        220                 225                 230 atg ttg ccc cag gcc ctt cat aac tac cta aca agt aaa ggg gtc act       892
Met Leu Pro Gln Ala Leu His Asn Tyr Leu Thr Ser Lys Gly Val Thr
235                 240                 245                 250 atc ctc agt ggt cag cca gcc tgc ggg ctc agc ctt cag cca gaa ggg       940
Ile Leu Ser Gly Gln Pro Ala Cys Gly Leu Ser Leu Gln Pro Glu Gly
                255                 260                 265 cac tgg aag gtg tct cta ggg gac agc agt ctg gag gct gac cac att       988
His Trp Lys Val Ser Leu Gly Asp Ser Ser Leu Glu Ala Asp His Ile
                270                 275                 280 ata agc acc att cca gct tca gtg ctc agc aag ctg ctc cct gcc gag      1036
Ile Ser Thr Ile Pro Ala Ser Val Leu Ser Lys Leu Leu Pro Ala Glu
            285                 290                 295 gct gca cct ctg gct cac atc ctg agt acc atc caa gct gtg tct gtg      1084
Ala Ala Pro Leu Ala His Ile Leu Ser Thr Ile Gln Ala Val Ser Val
        300                 305                 310 gcc gtg gtg aat ctg cag tac aaa gga gct tgt ctg cct gtg cag gga      1132
Ala Val Val Asn Leu Gln Tyr Lys Gly Ala Cys Leu Pro Val Gln Gly
315                 320                 325                 330 ttt gga cat ctg gtg cca tcc tca gaa gac ccg acc gtc ctg gga atc      1180
Phe Gly His Leu Val Pro Ser Ser Glu Asp Pro Thr Val Leu Gly Ile
                335                 340                 345 gtg tat gac tcg gtt gct ttt cct gag cag gat ggg aac ccc cca ggc      1228
Val Tyr Asp Ser Val Ala Phe Pro Glu Gln Asp Gly Asn Pro Pro Gly
                350                 355                 360 ctc aga ctg act gtg atg ttg gga ggt tac tgg tta cag aag ctg aaa      1276
Leu Arg Leu Thr Val Met Leu Gly Gly Tyr Trp Leu Gln Lys Leu Lys
            365                 370                 375 gcc aat ggc cat gaa ttg tct cca gag cta ttc caa cga gca gca cag      1324
Ala Asn Gly His Glu Leu Ser Pro Glu Leu Phe Gln Arg Ala Ala Gln
        380                 385                 390 gaa gcg gct gcc aca cag tta gga ctg aaa gag caa cca agc cat tgc      1372
Glu Ala Ala Ala Thr Gln Leu Gly Leu Lys Glu Gln Pro Ser His Cys
395                 400                 405                 410 ttg gtc cat cta cac aaa aac tgt atc cct cag tat aca cta ggc cac      1420
Leu Val His Leu His Lys Asn Cys Ile Pro Gln Tyr Thr Leu Gly His
                415                 420                 425 tgg caa aaa cta gac tca gct ctg caa ttc ctg acg gcc cag agg ttg      1468
Trp Gln Lys Leu Asp Ser Ala Leu Gln Phe Leu Thr Ala Gln Arg Leu
                430                 435                 440 ccc ctg act ttg gct ggg gcc tcc tat gag ggg gta gct gtc aat gac      1516
Pro Leu Thr Leu Ala Gly Ala Ser Tyr Glu Gly Val Ala Val Asn Asp
            445                 450                 455 tgt ata gag agt ggg cgc cag gca gca att gct gtc ctg ggc aca gaa      1564
Cys Ile Glu Ser Gly Arg Gln Ala Ala Ile Ala Val Leu Gly Thr Glu
        460                 465                 470 tcg aac agc tga ccccccactct cctactcatg aaagtaaaag ttgatggagc         1616
Ser Asn Ser
```

-continued

Ser Asn Ser
475 ttgaaaaaaa aaaaaaaaaa aa                                                1638

<210> SEQ ID NO 3
<211> LENGTH: 28
<212> TYPE: DNA
<213> ORGANISM: Artificial Sequence
<220> FEATURE:
<223> OTHER INFORMATION: Designed oligonucleotide primer used for
      amplifying a DNA
<223> OTHER INFORMATION: fragment containing a partial nucleotide
      sequence of a
<223> OTHER INFORMATION: rat-derived PPO gene

<400> SEQUENCE: 3
tttgcagagg agtgtttgct ggcaacag                                          28

<210> SEQ ID NO 4
<211> LENGTH: 29
<212> TYPE: DNA
<213> ORGANISM: Artificial Sequence
<220> FEATURE:
<223> OTHER INFORMATION: Designed oligonucleotide primer used for
      amplifying a DNA
<223> OTHER INFORMATION: fragment containing a partial nucleotide
      sequence of a
<223> OTHER INFORMATION: rat-derived PPO gene

<400> SEQUENCE: 4
agccgcttcc tgtgctgctc gttggaata                                         29

<210> SEQ ID NO 5
<211> LENGTH: 25
<212> TYPE: DNA
<213> ORGANISM: Artificial Sequence
<220> FEATURE:
<223> OTHER INFORMATION: Designed oligonucleotide primer used for
      constructing a
<223> OTHER INFORMATION: vector expressing a rat-derived PPO gene in
      Escherichia coli

<400> SEQUENCE: 5
aggccttacc gcggcccgga ctgtg                                             25

<210> SEQ ID NO 6
<211> LENGTH: 25
<212> TYPE: DNA
<213> ORGANISM: Artificial Sequence
<220> FEATURE:
<223> OTHER INFORMATION: Designed oligonucleotide primer used for
      constructing a
<223> OTHER INFORMATION: vector expressing a rat-derived PPO gene in
      Escherichia coli

<400> SEQUENCE: 6
taggagagcc cgggtcagat gttcg                                             25

<210> SEQ ID NO 7
<211> LENGTH: 25
<212> TYPE: DNA
<213> ORGANISM: Artificial Sequence
<220> FEATURE:
<223> OTHER INFORMATION: Designed oligonucleotide primer used for
      constructing a
<223> OTHER INFORMATION: rat-derived PPO gene expression vector for
      direct introduction
<223> OTHER INFORMATION: and a rat-derived PPO expression vector for
      indirect introduction

```
<400> SEQUENCE: 7
atggcccgga ctgtgatagt gcttg                                          25

<210> SEQ ID NO 8
<211> LENGTH: 25
<212> TYPE: DNA
<213> ORGANISM: Artificial Sequence
<220> FEATURE:
<223> OTHER INFORMATION: Designed oligonucleotide primer used for
      constructing a
<223> OTHER INFORMATION: rat-derived PPO gene expression vector for
      direct introduction
<223> OTHER INFORMATION: and a rat-derived PPO expression vector for
      indirect introduction

<400> SEQUENCE: 8
ttcatgagta ggagagtggg ggtca                                          25

<210> SEQ ID NO 9
<211> LENGTH: 563
<212> TYPE: PRT
<213> ORGANISM: Chlamydomonas reinhardtii CC-407

<400> SEQUENCE: 9
```

Met Met Leu Thr Gln Thr Pro Gly Thr Ala Thr Ala Ser Ser Arg Arg
 1               5                  10                  15

Ser Gln Ile Arg Ser Ala Ala His Val Ser Ala Lys Val Ala Pro Arg
                20                  25                  30

Pro Thr Pro Phe Ser Val Ala Ser Pro Ala Thr Ala Ala Ser Pro Ala
            35                  40                  45

Thr Ala Ala Arg Arg Thr Leu His Arg Thr Ala Ala Ala Ala Thr
        50                  55                  60

Gly Ala Pro Thr Ala Ser Gly Ala Gly Val Ala Lys Thr Leu Asp Asn
 65                  70                  75                  80

Val Tyr Asp Val Ile Val Val Gly Gly Leu Ser Gly Leu Val Thr
                85                  90                  95

Gly Gln Ala Leu Ala Ala Gln His Lys Ile Gln Asn Phe Leu Val Thr
            100                 105                 110

Glu Ala Arg Glu Arg Val Gly Gly Asn Ile Thr Ser Met Ser Gly Asp
        115                 120                 125

Gly Tyr Val Trp Glu Glu Gly Pro Asn Ser Phe Gln Pro Asn Asp Ser
    130                 135                 140

Met Leu Gln Ile Ala Val Asp Ser Gly Cys Glu Lys Asp Leu Val Phe
145                 150                 155                 160

Gly Asp Pro Thr Ala Pro Arg Phe Val Trp Glu Gly Lys Leu Arg
                165                 170                 175

Pro Val Pro Ser Gly Leu Asp Ala Phe Thr Phe Asp Leu Met Ser Ile
            180                 185                 190

Pro Gly Lys Ile Arg Ala Gly Leu Gly Ala Ile Gly Leu Ile Asn Gly
        195                 200                 205

Ala Met Pro Ser Phe Glu Glu Ser Val Glu Gln Phe Ile Arg Arg Asn
    210                 215                 220

Leu Gly Asp Glu Val Phe Phe Arg Leu Ile Glu Pro Phe Cys Ser Gly
225                 230                 235                 240

Val Tyr Ala Gly Asp Pro Ser Lys Leu Ser Met Lys Ala Ala Phe Asn
                245                 250                 255

Arg Ile Trp Ile Leu Glu Lys Asn Gly Gly Ser Leu Val Gly Gly Ala

```
                    260                 265                 270
Ile Lys Leu Phe Gln Glu Arg Gln Ser Asn Pro Ala Pro Pro Arg Asp
            275                 280                 285

Pro Arg Leu Pro Pro Lys Pro Lys Gly Gln Thr Val Gly Ser Phe Arg
        290                 295                 300

Lys Gly Leu Lys Met Leu Pro Asp Ala Ile Glu Arg Asn Ile Pro Asp
305                 310                 315                 320

Lys Ile Arg Val Asn Trp Lys Leu Val Ser Leu Gly Arg Glu Ala Asp
                325                 330                 335

Gly Arg Tyr Gly Leu Val Tyr Asp Thr Pro Glu Gly Arg Val Lys Val
            340                 345                 350

Phe Ala Arg Ala Val Ala Leu Thr Ala Pro Ser Tyr Val Val Ala Asp
        355                 360                 365

Leu Val Lys Glu Gln Ala Pro Ala Ala Glu Ala Leu Gly Ser Phe
370                 375                 380

Asp Tyr Pro Pro Val Gly Ala Val Thr Leu Ser Tyr Pro Leu Ser Ala
385                 390                 395                 400

Val Arg Glu Glu Arg Lys Ala Ser Asp Gly Ser Val Pro Gly Phe Gly
                405                 410                 415

Gln Leu His Pro Arg Thr Gln Gly Ile Thr Thr Leu Gly Thr Ile Tyr
            420                 425                 430

Ser Ser Ser Leu Phe Pro Gly Arg Ala Pro Glu Gly His Met Leu Leu
        435                 440                 445

Leu Asn Tyr Ile Gly Gly Thr Thr Asn Arg Gly Ile Val Asn Gln Thr
        450                 455                 460

Thr Glu Gln Leu Val Glu Gln Val Asp Lys Asp Leu Arg Asn Met Val
465                 470                 475                 480

Ile Lys Pro Asp Ala Pro Lys Pro Arg Val Val Gly Val Arg Val Trp
                485                 490                 495

Pro Arg Ala Ile Pro Gln Phe Asn Leu Gly His Leu Glu Gln Leu Asp
            500                 505                 510

Lys Ala Arg Lys Ala Leu Asp Ala Gly Leu Gln Gly Val His Leu
        515                 520                 525

Gly Gly Asn Tyr Val Ser Gly Val Ala Leu Gly Lys Val Val Glu His
        530                 535                 540

Gly Tyr Glu Ser Ala Ala Asn Leu Ala Lys Ser Val Ser Lys Ala Ala
545                 550                 555                 560

Val Lys Ala
        563

<210> SEQ ID NO 10
<211> LENGTH: 1838
<212> TYPE: DNA
<213> ORGANISM: Chlamydomonas reinhardtii CC-407
<220> FEATURE:
<222> LOCATION: (2)...(1793)

<400> SEQUENCE: 10 a atg atg ttg acc cag act cct ggg acc gcc acg gct tct agc cgg     46
  Met Met Leu Thr Gln Thr Pro Gly Thr Ala Thr Ala Ser Ser Arg
  1               5                   10                  15 cgg tcg cag atc cgc tcg gct gcg cac gtc tcc gcc aag gtc gcg cct    94
Arg Ser Gln Ile Arg Ser Ala Ala His Val Ser Ala Lys Val Ala Pro
                20                  25                  30 cgg ccc acg cca ttc tcg gtc gcg agc ccc gcg acc gct gcg agc ccc   142
Arg Pro Thr Pro Phe Ser Val Ala Ser Pro Ala Thr Ala Ala Ser Pro
```

-continued

|  |  |  |  |  |  |  |  |  |  |  |  |  |  |  |  |
|---|---|---|---|---|---|---|---|---|---|---|---|---|---|---|---|
|  |  | 35 |  |  |  | 40 |  |  |  | 45 |  |  |  |  |  |
| gcg | acc | gcg | gcg | gcc | cgc | cgc | aca | ctc | cac | cgc | act | gct | gcg | gcg | gcc | 190 |
| Ala | Thr | Ala | Ala | Ala | Arg | Arg | Thr | Leu | His | Arg | Thr | Ala | Ala | Ala | Ala |  |
|  | 50 |  |  |  |  | 55 |  |  |  |  | 60 |  |  |  |  |  |
| act | ggt | gct | ccc | acg | gcg | tcc | gga | gcc | ggc | gtc | gcc | aag | acg | ctc | gac | 238 |
| Thr | Gly | Ala | Pro | Thr | Ala | Ser | Gly | Ala | Gly | Val | Ala | Lys | Thr | Leu | Asp |  |
|  | 65 |  |  |  |  | 70 |  |  |  |  | 75 |  |  |  |  |  |
| aat | gtg | tat | gac | gtg | atc | gtg | gtc | ggt | gga | ggt | ctc | tcg | ggc | ctg | gtg | 286 |
| Asn | Val | Tyr | Asp | Val | Ile | Val | Val | Gly | Gly | Gly | Leu | Ser | Gly | Leu | Val |  |
| 80 |  |  |  |  | 85 |  |  |  |  | 90 |  |  |  |  | 95 |  |
| acc | ggc | cag | gcc | ctg | gcg | gct | cag | cac | aaa | att | cag | aac | ttc | ctt | gtt | 334 |
| Thr | Gly | Gln | Ala | Leu | Ala | Ala | Gln | His | Lys | Ile | Gln | Asn | Phe | Leu | Val |  |
|  |  |  |  | 100 |  |  |  |  | 105 |  |  |  |  | 110 |  |  |
| acg | gag | gct | cgc | gag | cgc | gtc | ggc | ggc | aac | att | acg | tcc | atg | tcg | ggc | 382 |
| Thr | Glu | Ala | Arg | Glu | Arg | Val | Gly | Gly | Asn | Ile | Thr | Ser | Met | Ser | Gly |  |
|  |  |  | 115 |  |  |  |  | 120 |  |  |  |  | 125 |  |  |  |
| gat | ggc | tac | gtg | tgg | gag | gag | ggc | ccg | aac | agc | ttc | cag | ccc | aac | gat | 430 |
| Asp | Gly | Tyr | Val | Trp | Glu | Glu | Gly | Pro | Asn | Ser | Phe | Gln | Pro | Asn | Asp |  |
|  |  | 130 |  |  |  |  | 135 |  |  |  |  | 140 |  |  |  |  |
| agc | atg | ctg | cag | att | gcg | gtg | gac | tct | ggc | tgc | gag | aag | gac | ctt | gtg | 478 |
| Ser | Met | Leu | Gln | Ile | Ala | Val | Asp | Ser | Gly | Cys | Glu | Lys | Asp | Leu | Val |  |
|  | 145 |  |  |  |  | 150 |  |  |  |  | 155 |  |  |  |  |  |
| ttc | ggt | gac | ccc | acg | gct | ccc | cgc | ttc | gtg | tgg | tgg | gag | ggc | aag | ctg | 526 |
| Phe | Gly | Asp | Pro | Thr | Ala | Pro | Arg | Phe | Val | Trp | Trp | Glu | Gly | Lys | Leu |  |
| 160 |  |  |  |  | 165 |  |  |  |  | 170 |  |  |  |  | 175 |  |
| cgc | ccc | gtg | ccc | tcg | ggc | ctg | gac | gcc | ttc | acc | ttc | gac | ctc | atg | tcc | 574 |
| Arg | Pro | Val | Pro | Ser | Gly | Leu | Asp | Ala | Phe | Thr | Phe | Asp | Leu | Met | Ser |  |
|  |  |  |  | 180 |  |  |  |  | 185 |  |  |  |  | 190 |  |  |
| atc | ccc | ggc | aag | atc | cgc | gcc | ggg | ctg | ggc | gcc | atc | ggc | ctc | atc | aac | 622 |
| Ile | Pro | Gly | Lys | Ile | Arg | Ala | Gly | Leu | Gly | Ala | Ile | Gly | Leu | Ile | Asn |  |
|  |  |  | 195 |  |  |  |  | 200 |  |  |  |  | 205 |  |  |  |
| gga | gcc | atg | ccc | tcc | ttc | gag | gag | agt | gtg | gag | cag | ttc | atc | cgc | cgc | 670 |
| Gly | Ala | Met | Pro | Ser | Phe | Glu | Glu | Ser | Val | Glu | Gln | Phe | Ile | Arg | Arg |  |
|  |  | 210 |  |  |  |  | 215 |  |  |  |  | 220 |  |  |  |  |
| aac | ctg | ggc | gat | gag | gtg | ttc | ttc | cgc | ctg | atc | gag | ccc | ttc | tgc | tcc | 718 |
| Asn | Leu | Gly | Asp | Glu | Val | Phe | Phe | Arg | Leu | Ile | Glu | Pro | Phe | Cys | Ser |  |
|  | 225 |  |  |  |  | 230 |  |  |  |  | 235 |  |  |  |  |  |
| ggc | gtg | tac | gcg | ggc | gac | ccc | tcc | aag | ctg | tcc | atg | aag | gcg | gcc | ttc | 766 |
| Gly | Val | Tyr | Ala | Gly | Asp | Pro | Ser | Lys | Leu | Ser | Met | Lys | Ala | Ala | Phe |  |
| 240 |  |  |  |  | 245 |  |  |  |  | 250 |  |  |  |  | 255 |  |
| aac | agg | atc | tgg | att | ctg | gag | aag | aac | ggc | ggc | agc | ctg | gtg | gga | ggt | 814 |
| Asn | Arg | Ile | Trp | Ile | Leu | Glu | Lys | Asn | Gly | Gly | Ser | Leu | Val | Gly | Gly |  |
|  |  |  | 260 |  |  |  |  | 265 |  |  |  |  | 270 |  |  |  |
| gcc | atc | aag | ctg | ttc | cag | gaa | cgc | cag | tcc | aac | ccg | gcc | ccg | ccg | cgg | 862 |
| Ala | Ile | Lys | Leu | Phe | Gln | Glu | Arg | Gln | Ser | Asn | Pro | Ala | Pro | Pro | Arg |  |
|  |  | 275 |  |  |  |  | 280 |  |  |  |  | 285 |  |  |  |  |
| gac | ccg | cgc | ctg | ccg | ccc | aag | ccc | aag | ggc | cag | acg | gtg | ggc | tcg | ttc | 910 |
| Asp | Pro | Arg | Leu | Pro | Pro | Lys | Pro | Lys | Gly | Gln | Thr | Val | Gly | Ser | Phe |  |
|  | 290 |  |  |  |  | 295 |  |  |  |  | 300 |  |  |  |  |  |
| cgc | aag | ggc | ctg | aag | atg | ctg | ccg | gac | gcc | att | gag | cgc | aac | atc | ccc | 958 |
| Arg | Lys | Gly | Leu | Lys | Met | Leu | Pro | Asp | Ala | Ile | Glu | Arg | Asn | Ile | Pro |  |
| 305 |  |  |  |  | 310 |  |  |  |  | 315 |  |  |  |  |  |  |
| gac | aag | atc | cgc | gtg | aac | tgg | aag | ctg | gtg | tct | ctg | ggc | cgc | gag | gcg | 1006 |
| Asp | Lys | Ile | Arg | Val | Asn | Trp | Lys | Leu | Val | Ser | Leu | Gly | Arg | Glu | Ala |  |
| 320 |  |  |  |  | 325 |  |  |  |  | 330 |  |  |  |  | 335 |  |
| gac | ggg | cgg | tac | ggg | ctg | gtg | tac | gac | acg | ccc | gag | ggc | cgt | gtc | aag | 1054 |
| Asp | Gly | Arg | Tyr | Gly | Leu | Val | Tyr | Asp | Thr | Pro | Glu | Gly | Arg | Val | Lys |  |
|  |  |  | 340 |  |  |  |  | 345 |  |  |  |  | 350 |  |  |  |
| gtg | ttt | gcc | cgc | gcc | gtg | gct | ctg | acc | gcg | ccc | agc | tac | gtg | gtg | gcg | 1102 |

```
                Val Phe Ala Arg Ala Val Ala Leu Thr Ala Pro Ser Tyr Val Val Ala
                            355                 360                 365 gac ctg gtc aag gag cag gcg ccc gcc gcc gcc gag gcc ctg ggc tcc          1150
Asp Leu Val Lys Glu Gln Ala Pro Ala Ala Ala Glu Ala Leu Gly Ser
            370                 375                 380 ttc gac tac ccg ccg gtg ggc gcc gtg acg ctg tcg tac ccg ctg agc          1198
Phe Asp Tyr Pro Pro Val Gly Ala Val Thr Leu Ser Tyr Pro Leu Ser
385                 390                 395 gcc gtg cgg gag gag cgc aag gcc tcg gac ggg tcc gtg ccg ggc ttc          1246
Ala Val Arg Glu Glu Arg Lys Ala Ser Asp Gly Ser Val Pro Gly Phe
400                 405                 410                 415 ggt cag ctg cac ccg cgc acg cag ggc atc acc act ctg ggc acc atc          1294
Gly Gln Leu His Pro Arg Thr Gln Gly Ile Thr Thr Leu Gly Thr Ile
                420                 425                 430 tac agc tcc agc ctg ttc ccc ggc cgc gcg ccc gag ggc cac atg ctg          1342
Tyr Ser Ser Ser Leu Phe Pro Gly Arg Ala Pro Glu Gly His Met Leu
            435                 440                 445 ctg ctc aac tac atc ggc ggc acc acc aac cgc ggc atc gtc aac cag          1390
Leu Leu Asn Tyr Ile Gly Gly Thr Thr Asn Arg Gly Ile Val Asn Gln
        450                 455                 460 acc acc gag cag ctg gtg gag cag gtg gac aag gac ctg cgc aac atg          1438
Thr Thr Glu Gln Leu Val Glu Gln Val Asp Lys Asp Leu Arg Asn Met
465                 470                 475 gtc atc aag ccc gac gcg ccc aag ccc cgt gtg gtg ggc gtg cgc gtg          1486
Val Ile Lys Pro Asp Ala Pro Lys Pro Arg Val Val Gly Val Arg Val
480                 485                 490                 495 tgg ccg cgc gcc atc ccg cag ttc aac ctg ggc cac ctg gag cag ctg          1534
Trp Pro Arg Ala Ile Pro Gln Phe Asn Leu Gly His Leu Glu Gln Leu
                500                 505                 510 gac aag gcg cgc aag gcg ctg gac gcg gcg ggg ctg cag ggc gtg cac          1582
Asp Lys Ala Arg Lys Ala Leu Asp Ala Ala Gly Leu Gln Gly Val His
            515                 520                 525 ctg ggg ggc aac tac gtc agc ggt gtg gcc ctg ggc aag gtg gtg gag          1630
Leu Gly Gly Asn Tyr Val Ser Gly Val Ala Leu Gly Lys Val Val Glu
        530                 535                 540 cac ggc tac gag tcc gca gcc aac ctg gcc aag agc gtg tcc aag gcc          1678
His Gly Tyr Glu Ser Ala Ala Asn Leu Ala Lys Ser Val Ser Lys Ala
545                 550                 555 gca gtc aag gcc taa gcggctgcag cagtagcagc agcagcatcg ggctgtagct         1733
Ala Val Lys Ala
560         563 ggtaaatgcc gcagtggcac cggcagcagc aattggcaag cacttggggc aagcggagtg        1793
gaggcgaggg gggggctacc attggcgctt gctgggatgt gtagt                        1838
```

<210> SEQ ID NO 11
<211> LENGTH: 28
<212> TYPE: DNA
<213> ORGANISM: Artificial Sequence
<220> FEATURE:
<223> OTHER INFORMATION: Designed oligonucleotide primer used for
      amplifying a DNA
<223> OTHER INFORMATION: fragment containing a Chlamydomonas reinhardtii
      -derived PPO gene

<400> SEQUENCE: 11
aatgatgttg acccagactc ctgggacc                                            28

<210> SEQ ID NO 12
<211> LENGTH: 27
<212> TYPE: DNA

```
<213> ORGANISM: Artificial Sequence
<220> FEATURE:
<223> OTHER INFORMATION: Designed oligonucleotide primer used for
      constructing a
<223> OTHER INFORMATION: vector for expressing a Chlamydomonas
      reinhardtii-derived
<223> OTHER INFORMATION: PPO gene in Escherichia coli

<400> SEQUENCE: 12
tactacacat cccagcaagc gccaatg                                          27

<210> SEQ ID NO 13
<211> LENGTH: 32
<212> TYPE: DNA
<213> ORGANISM: Artificial Sequence
<220> FEATURE:
<223> OTHER INFORMATION: Designed oligonucleotide primer used for
      constructing a
<223> OTHER INFORMATION: vector for expressing a Chlamydomonas
      reinhardtii-derived PPO gene in
<223> OTHER INFORMATION: Escherichia coli

<400> SEQUENCE: 13
tcgagctcaa tgatgttgac ccagactcct gg                                    32

<210> SEQ ID NO 14
<211> LENGTH: 32
<212> TYPE: DNA
<213> ORGANISM: Artificial Sequence
<220> FEATURE:
<223> OTHER INFORMATION: Designed oligonucleotide primer used for
      constructing a
<223> OTHER INFORMATION: vector for expressing a Chlamydomonas
      reinhardtii-derived
<223> OTHER INFORMATION: PPO gene in Escherichia coli

<400> SEQUENCE: 14
ttgtcgacta ctacacatcc cagcaagcgc ca                                    32
```

METHOD FOR EVALUATING THE ABILITY OF A COMPOUND TO INHIBIT THE PROTOPORPHYRINOGEN OXIDASE ACTIVITY

BACKGROUND OF THE INVENTION

1. Field of the Invention

The present invention relates to a method for evaluating the ability of a compound to inhibit the protoporphyrinogen oxidase activity.

2. Description of the Related Art

Plants, animals and microorganisms possess the porphyrin biosynthetic system starting with 5-aminolevulinic acid and produce protoporphyrin which is a precursor for the heme biosynthesis and the like. An enzyme which catalyses a reaction oxidizing protoporphyrinogen at the final stage of the porphyrin biosynthesis to produce protoporphyrin is protoporphyrinogen oxidase (protoporphyrinogen IX oxidase; EC 1.3.3.4)(hereinafter referred to as "PPO")(R. J. Porra and J. E. Falk, (1964) Biochem. J., Vol.90, pp.69–75).

The PPO activity has the influence on the growth of plants, animals and microorganisms and it is known that compounds which inhibit the plant-derived PPO activity have generally the herbicidal activity. Thus, in order to effectively develop PPO inhibiting-type herbicides, there has been a need for a method for evaluating the ability of a compound to inhibit the PPO activity with simplicity.

SUMMARY OF THE INVENTION

Under the aforementioned circumstances, the present inventors studied hard, which resulted in completion of the present invention.

The present invention provides:

1. A method for evaluating the ability of a compound to inhibit the protoporphyrinogen oxidase activity, which comprises the steps of:
   (1) culturing a transformant expressing a protoporphyrinogen oxidase gene present in a DNA fragment in a medium containing substantially no protoheme compounds in each comparative system of the presence and absence of a test compound to measure a growth rate of the transformant under each condition, said transformant being resulted from a host cell deficient in the growing ability based on the protoporphyrinogen oxidase activity transformed with the DNA fragment in which a promoter functionable in the host cell and a protoporphyrinogen oxidase gene are operatively linked, and
   (2) determining the ability of the compound to inhibit the protoporphyrinogen oxidase activity by comparing the growth rates (hereinafter refered to as "the present method").

2. A method for evaluating the ability of a compound to inhibit the protoporphyrinogen oxidase activity, which comprises the steps of:
   (1) culturing a transformant expressing a protoporphyrinogen oxidase gene present in a DNA fragment in a medium containing substantially no protoheme compounds in each comparative system of the presence and absence of a test compound to measure a growth rate of the transformant under each condition, said transformant being resulted from a host cell deficient in the growing ability based on the protoporphyrinogen oxidase activity transformed with the DNA fragment in which a promoter functionable in the host cell, a protoporphyrinogen oxidase gene and a terminator functionable in the host cell are operatively linked, and
   (2) determining the ability of the compound to inhibit the protoporphyrinogen oxidase activity by comparing the growth rates.

3. A method for evaluating the ability of a compound to inhibit the protoporphyrinogen oxidase activity, which comprises the steps of:
   (1) culturing a transformant expressing a protoporphyrinogen oxidase gene present in the following (a) DNA fragment in a medium containing substantially no protoheme compounds in each comparative system of the presence and absence of a test compound to measure a growth rate of the transformant under each condition, said transformant being resulted from a host cell deficient in the growing ability based on protoporphyrinogen oxidase activity transformed with
      (a) the DNA fragment in which a promoter functionable in the host cell and controllable in its transcriptional activity, and a protoporphyrinogen oxidase gene are operatively linked, and
      (b) a DNA fragment in which a gene being capable of controlling the transcriptional activity of the promoter in the above DNA fragment and a promoter having the transcriptional activity not controllable by the gene and functionable in the host cell are operatively linked, and
   (2) determining the ability of the compound to inhibit the protoporphyrinogen oxidase activity by comparing the growth rates.

4. A method for evaluating the ability of a compound to inhibit the protoporphyrinogen oxidase activity, which comprises the steps of:
   (1) culturing a transformant expressing a protoporphyrinogen oxidase gene present in the following (a) DNA fragment in a medium containing substantially no protoheme compounds in each comparative system of the presence and absence of a test compound to measure a growth rate of the transformant under each condition, said transformant being resulted from a host cell deficient in the growing ability based on the protoporphyrinogen oxidase activity transformed with
      (a) the DNA fragment in which a promoter functionable in the host cell and controllable in its transcriptional activity, a protoporphyrinogen oxidase gene and a terminator functionable in the host cell are operatively linked, and
      (b) a DNA fragment in which a gene being capable of controlling the transcriptional activity of the promoter in the above DNA fragment, a promoter having the transcriptional activity not controllable by the gene and functionable in the host cell, and a terminator functionable in the host cell are operatively linked, and
   (2) determining the ability of the compound to inhibit the protoporphyrinogen oxidase activity by comparing the growth rates.

5. The method according to 1 or 3, which is characterized in that the protoporphyrinogen oxidase gene is a protoporphyrinogen oxidase gene derived from an animal or a plant.

6. The method according to 1 or 3, which is characterized in that the protoporphyrinogen oxidase gene is a protoporphyrinogen oxidase gene derived from a rat or *Chlamydomonas reinhardtii*.

7. The method according to 1 or 3, which is characterized in that the host cell is a microorganism.

8. A rat-derived gene encoding a protein having the protoporphyrinogen oxidase activity.

9. A protoporphyrinogen oxidase gene encoding a protein having the amino acid sequence shown by SEQ ID: No.1.

10. A gene encoding a protein having the protoporphyrinogen oxidase activity and having the amino acid sequence in which one or several amino acids are deleted, substituted, modified or added in the amino acid sequence shown by SEQ ID: No.1.

11. A protoporphyrinogen oxidase gene having the nucleotide sequence encoding the amino acid sequence shown by SEQ ID: No.1.

12. A protoporphyrinogen oxidase gene having the nucleotide sequence shown by SEQ ID: No.2.

13. A DNA fragment having a partial nucleotide sequence of the protoporphyrinogen oxidase gene of any one of 8 to 12.

14. A vector which comprises the protoporphyrinogen oxidase gene of any one of 8 to 12.

15. A transformant which is characterized in that the vector of 14 is introduced in to a host cell.

16. The transformant according to 15, wherein the host cell is a microorganism.

17. The transformant according to 15, wherein the host cell is a plant.

18. A *Chlamydomonas reinhardtii*-derived gene encoding a protein having the protoporphyrinogen oxidase activity.

19. A protoporphyrinogen oxidase gene encoding a protein having the amino acid sequence shown by SEQ ID: No.9.

20. A gene encoding a protein having the protoporphyrinogen oxidase activity and having the amino acid sequence in which one or several amino acids are deleted, substituted, modified or added in the amino acid sequence shown by SEQ ID: No.9.

21. A protoporphyrinogen oxidase gene having the nucleotide sequence encoding the amino acid sequence shown by SEQ ID: No.9.

22. A protoporphyrinogen oxidase gene having the nucleotide sequence shown by SEQ ID: No.10.

23. A DNA fragment having a partial nucleotide sequence of the protoporphyrinogen oxidase gene of any one of 18 to 22.

24. A vector which comprises the protoporphyrinogen oxidase gene of any one of 18 to 22.

25. A transformant which is characterized in that the vector of 24 is introduced in a host cell.

26. The transformant according to 25, wherein the host cell is a microorganism.

27. The transformant according to 25, wherein the host cell is a plant.

[PPO fragment 1] shows a DNA fragment obtained by a polymerase chain reaction of Example 2, [PPO fragment 2] shows a DNA fragment harbored by a clone obtained in Example 1, [PPO] shows a rat-derived protoporphyrinogen oxidase cDNA, and other symbols show a restriction enzyme recognition site.

Figure 1:
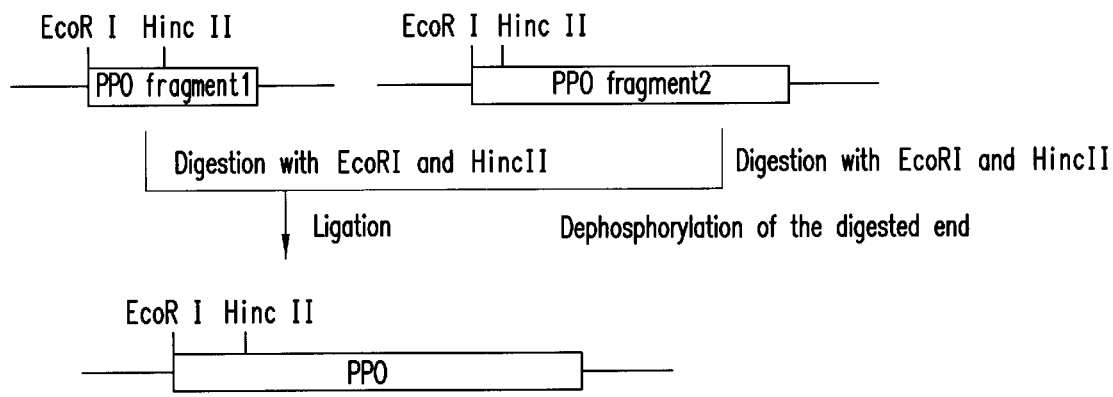
FIG. 1 shows a method for constructing a vector containing a full length rat-derived protoporphyrinogen oxidase cDNA.
Figure 2:
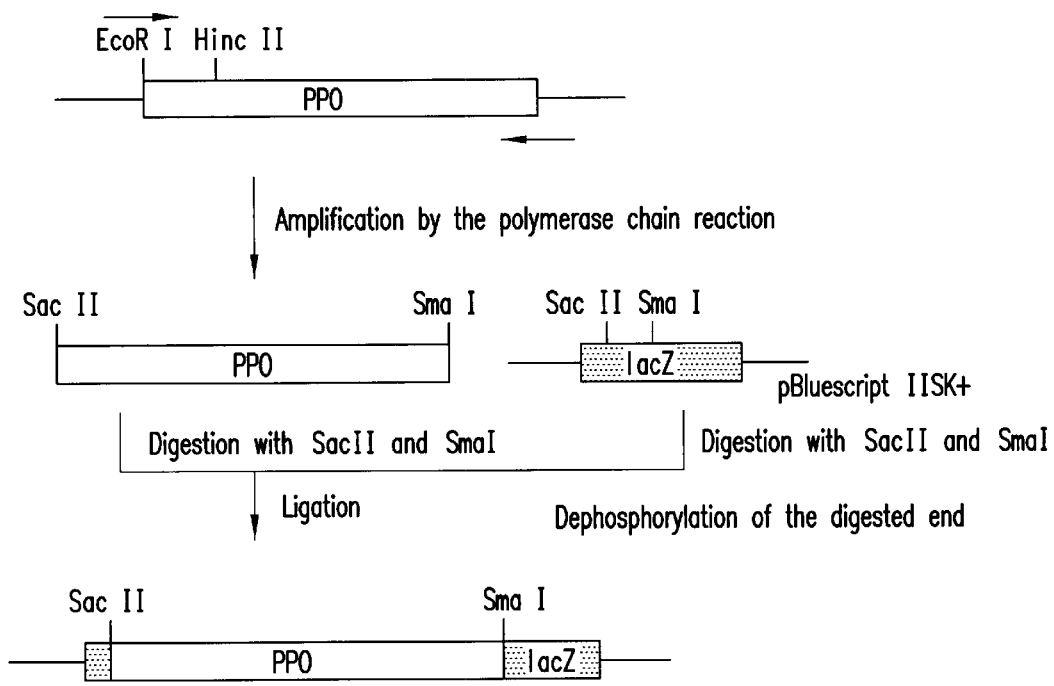

FIG. 2 shows a method for constructing a protoporphyrinogen expression vector which is constructed for expressing a rat-derived protoporphyrinogen oxidase by introducing it into *Escherichia coli*.

[PPO] shows a rat-derived protoporphyrinogen oxidase cDNA, [lacZ] shows a beta-galactosidase gene, and other symbols show a restriction enzyme recognition site.

Figure 3:
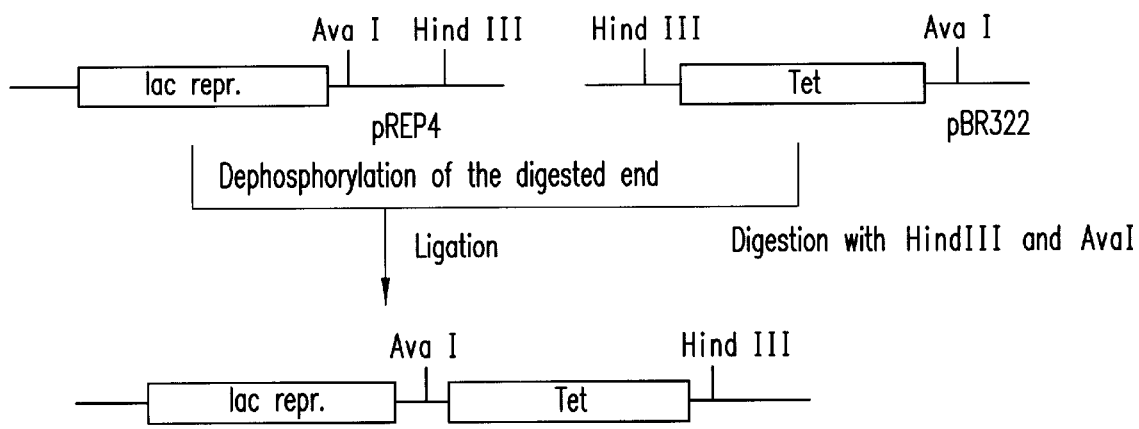

FIG. 3 shows a method for constructing a lac repressor expression vector which is constructed for expressing a lac repressor by introducing it into *Escherichia coli*.

Figure 4:
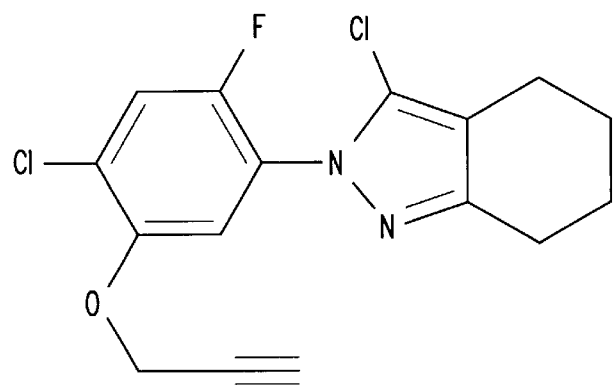

FIG. 4 shows the structure of a compound which was subjected to a test on the ability of a compound to inhibit the rat-derived protoporphyrinogen oxidase activity.

Figure 5:
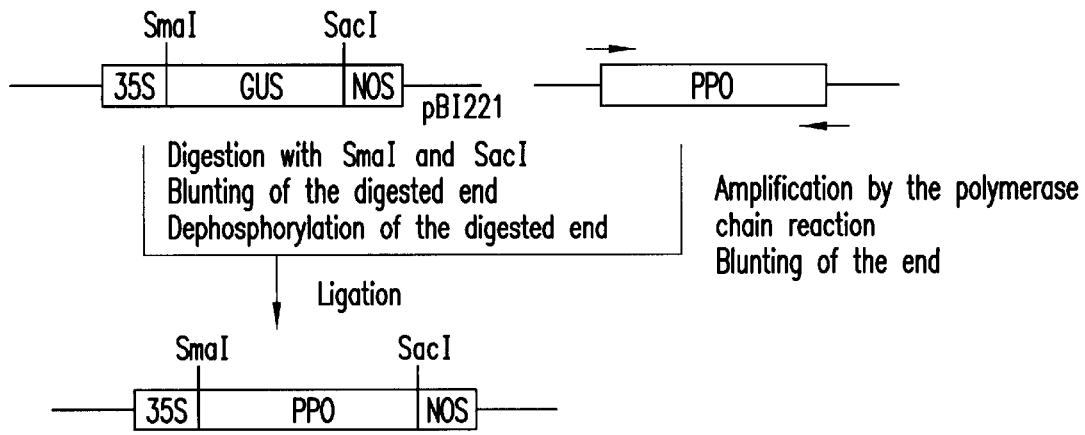

FIG. 5 shows a method for constructing a protoporphyrinogen oxidase expression vector for direct introduction which is constructed for expressing a rat-derived protoporphyrinogen oxidase by introducing it into a plant cell.

[35S] shows the cauliflower mosaic virus-derived 35S promoter, [NOS] shows the Agrobacterium-derived nopaline synthase terminator, [PPO] shows a rat-derived protoporphyrinogen oxidase cDNA, and other symbols show a restriction enzyme recognition site.

Figure 6:
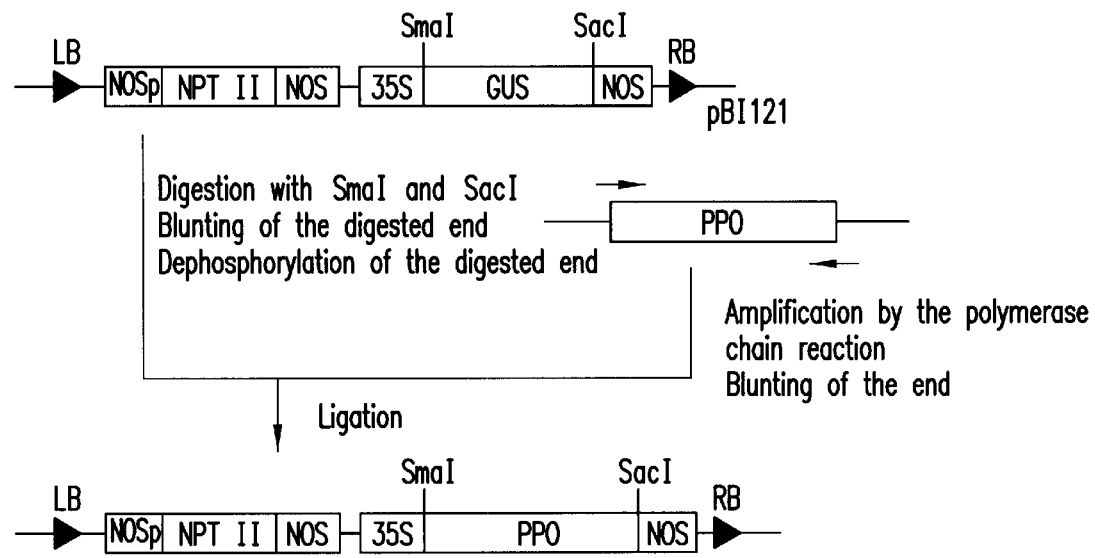

FIG. 6 shows a method for constructing a protoporphyrinogen oxidase expression vector for indirect introduction which is constructed for a rat-derived protoporphyrinogen oxidase by introducing it into a plant cell.

[35S] shows the cauliflower mosaic virus-derived 35S promoter, [NOS] shows the Agrobaceturm-derived nopaline synthase terminator, [PPO] shows a rat-derived protoporphyrinogen oxidase cDNA, [NTPII] shows a kanamycin-resistant gene, [NOSp] shows the Agrobaceturm-derived nopaline synthase promoter, [LB] and [RB] show the Agrobaceturm T-DNA-derived left border nucleotide sequence and right border nucleotide sequence, respectively, and other symbols show a restriction enzyme recognition site.

DETAILED DESCRIPTION OF THE PREFERRED EMBODIMENT

The present invention will be described in detail.

First, the present method will be described.

A PPO gene used in the present method may be any ones encoding a protein having the PPO activity upon expression in the host cell and, for example, may be selected from PPO genes derived from plants and animals. More particularly, there are PPO genes derived from Dicotyledonous plants such as Arabidopsis, soybean, oil seed rape, sugar beat, potato and tobacco, Monocotyledonous plants such as corn, rice, wheat, barley, oat, rye, sugar cane and sorghum, algae such as *Chlamydomonas reinhardtii* and Chlorella, mammals such as mouse, rat and human, fishes sich as trout, bluegill, carp, cyprinodont, guppy, zebra fish and fathead minnow, insects such as fly, mosquito, cockroach, greasy grind, dragonfly and silkworm moth.

As used herein, "a promoter functionable in a host cell" used in the present method is a DNA fragment having the transcriptional activity in a host cell being transformed and includes, for example, *Escherichia coli* lactose operon promoter (lacP), tryptophan operon promoter (trpP), arginine operon promoter (argP), galactose operon promoter (galP), tac promoter, T7 promoter, T3 promoter, λ phage promoter (λ-pL, λ-pR), yeast alcohol dehydrogenase gene (ADH) promoter, adenovirus major late (Ad.ML) promoter, SV40 early promoter, baculovirus promoter, nopaline synthase gene (NOS) promoter, octopine synthase gene (OCT) promoter, cauliflower mosaic virus (CaMV)-derived 19S and 35S promoters, phenylalanine ammonia lyase (PAL) gene promoter, chalcone synthase (CHS) gene promoter and the like.

In addition, "a terminator functionable in a host cell" used if necessary includes any DNA fragments having the transcription terminating activity in a host cell being transformed. Examples thereof include *Escherichia coli* lactose operon terminator, arginine operon terminator, galactose operon terminator, yeast HIS terminator, ADH1 terminator, SV40 early splicing region, nopaline synthase gene (NOS) terminator, garlic virus GV1 and GV2 terminators and the like.

As used herein, "a DNA fragment are operatively linked" means a DNA fragment in which these promoter, and, if necessary, these terminator, are linked so that the above PPO gene is expressed under the control of the above promoter, and, if necessary, the above terminator, in a host cell into which they are to be introduced (hereinafter referred to as "expression DNA fragment").

The above expression DNA fragment is introduced into a host cell deficient in the growing ability based on the PPO activity to obtain a transformant expressing the introduced PPO gene.

A host cell being transformed, that is, deficient in the growing ability based on the PPO activity may be any host cells deficient in the PPO activity necessary for growth and, from a viewpoint of simple culturing, microorganisms are preferable. Examples of microorganisms deficient in the PPO activity necessary for growth include PPO gene (hemG locus)-deficient mutant *Escherichia coli* strain VSR 751 described in K. Miyamoto, K. Nakahigashi, K. Nishimura, T. Nakayashiki and H. Inokuchi, (1991) Journal of Molecular Biology, vol.219, pp393–398 and K. Nishimura, T. Nakayashiki and H. Inokuchi, (1993) Gene, vol.133, pp109–113, PPO gene (hemG locus)-deficient mutant *Escherichia coli* strain BT3 described in F. Yamamoto, H. Inokuchi and H. Ozeki, (1988) Jpn. J. Genet., vol.63, pp237–249, PPO gene (hem14-1 locus)-deficient mutant yeast strain hem14-1 described in J. M. Gamadro, D. Urban-Grimal and P. Labbe (1982) Biochem. Biophys. Res. Commun., vol.106, pp724–730, and the like.

The above expression DNA fragment incorporated into a vector may be introduced into a host cell. The vector containing the expression DNA fragment may be introduced into a host cell according to the conventional genetic engineering method. For example, when the host cell is a microorganism, the vector may be introduced into a cell of the microorganism with a calcium chloride method, an electroporation method (Methods in Electroporation: Gene Pulser/*E. coli* Pulser System, Bio-Rad Laboratories, 1993) and the like. In addition, when the host cell is a plant, the vector may be introduced into a cell of the plant with an Agrobacterium infection method (JP-B-2-58917 (examined) and JP-A-60-70080 (laid-opened)), an electroporation into a protoplast method (JP-A-60-251887 (laid-opened) and JP-A-5-68575 (laid-opened)), a particle gun method (JP-A-5-508316 (laid-opened) and JP-A-63-258525 (laid-opened)) and the like. A transformant expressing the introduced PPO gene may be obtained by culturing the host cell with the introduced vector in a medium containing a growth inhibitor corresponding to a selectable marker lucus-linked on the vector and a medium containing substantially no protoheme compounds, and isolating a clone which can grow in the medium.

The transformant thus obtained is first cultured in a medium containing substantially no protoheme compounds in each comparative system of the presence at a variety of concentrations and absence of a test compound to measure a growth rate of the transformant under each condition. Next, the PPO activity inhibiting ability of the test compound to inhibit the PPO activity is determined by comparing the growth rates based on the each comparative system of contact and non-contact of the transformant and the test compound. The comparison of the growth rates is performed, for example, by obtaining the growth inhibiting rate by calculating a ratio of the growth rate in a system of the presence of the test compound relative to the growth rate in a system of the absence of the test compound, and comparing the growth inhibiting rates regarding a plurality of test compounds and, based on the results thereof, the higher or lower ability for inhibiting PPO activity may be determined. More particularly, for example, a concentration of a test compound at which the growth is inhibited by 50% is obtained from the growth rate of the transformant in the system of the addition of a compound (that is, of the presence of the test compound) under the conditions that the growth rate of the transformant is 100% in the system of no addition of a compound (that is, of the absence of the test compound). The test compound having the lower concentration may be determined to be higher in the ability for inhibiting PPO activity than the test compound having the higher concentration. Alternatively, a compound known to inhibit the PPO activity (positive control) is simultaneously subjected to an experiment as one of test compounds, which may serve as an index for the growth inhibiting rate of each test compound (for example, a compound concentration at which the growth is inhibited by 50%).

As used herein, "a medium containing substantially no protoheme compounds" means a medium not containing any protoheme compounds or a medium which may contain protoheme compounds at such an amount that a host cell deficient in the growing ability based on the PPO activity can not recover the growing ability to the same level as that of the corresponding non-deficient host cell (that is, a host cell not deficient in the growing ability based on the PPO activity) regardless of the presence of protoheme compounds in the medium. The examples thereof include an artificial medium not containing any protoheme compounds such as protoporphyrin, protohemin and the like at all, a medium containing natural extracts (for example, yeast extract, Malt extract and the like), and the like. From a viewpoint of the precision of the present method, it is preferable that an amount of the protoheme compounds present in a medium is zero or as low as possible. In addition, protoheme compounds include protoheme and its derivatives and these compounds mean a compound having the action of recovering the growing ability of a host cell deficient in the growing ability based on the PPO activity.

In order to confirm that the growth inhibition by a test compound is due to the inhibition of PPO activity, it can be easily determined by performing the culturing of the above transformant in a medium containing substantially protoheme compounds such as protoporphyrin, protohemin and the like, and confirming the growth of the transformant. In addition, if needed, the growth rate of the transformant may be conveniently adjusted by the relationship between an expressed amount of PPO gene and a concentration of a test compound.

In the present method, the expressed amount of PPO gene in the transformant may vary by using "a promoter functionable in a host cell and controllable in its transcriptional activity" as a promoter for the aforementioned expression DNA fragment, and introducing into the host cell "a DNA fragment in which a gene capable of controlling the transcriptional activity of a promoter in the expression DNA fragment and a promoter having the transcriptional activity not-controllable by the gene and functionable in the host cell, and an optionally used terminator functionable in the host cell are operatively linked" (hereinafter referred to as "regulatory DNA fragment"). For example, when evaluation of a test compound having the lower water-solubility and that of a small amount of a test compound are performed, by adjusting an expressed amount of PPO gene in the transformant to be small, evaluation may be performed with the higher precision.

On the other hand, when evaluation of a test compound having the higher ability for inhibiting PPO activity are performed, by adjusting an expressed amount of PPO gene in the transformant to be increased, evaluation may be performed with the higher precision.

As used herein, "a gene capable of controlling the transcriptional activity of a promoter in the expression DNA fragment"(hereinafter referred to as "a regulatory gene") means a gene having the function of inhibiting or promoting the transcriptional activity of "a promoter functionable in the host cell and controllable in its transcriptional activity" as a promoter for the expression DNA fragment. When an expressed amount of PPO gene is to be decreased, a gene which inhibits the transcriptional activity of a promoter in the expression DNA fragment may be used, while when an expressed amount of PPO gene is to be increased, a gene which promotes the transcriptional activity of the promoter may be used. More particularly, examples of a combination for inhibiting the transcriptional activity include a combination of *Escherichia coli* lactose operon promoter and lacI, that of arginine operon promoter and argR, that of galactose operon promoter and GalR and the like. On the other hand, examples of a combination for promoting the transcriptional activity include a combination of *Escherichia coli* lactose operon promoter and crp, that of *Klebsiella pneumoniae* maltose regulon and malT and the like.

"A promoter having the transcriptional activity not-controllable by the regulatory gene and functionable in a host cell", that is, a promoter for the regulatory DNA fragment may be any promoters having no influence by a gene which they themselves control. For example, in a case of a promoer to be combined with a repressor gene for the above lactose operon, its own promoter, nopaline synthase enzyme gene (NOS) promoter and the like may be used.

The above expression DNA fragment and the regulatory DNA fragment may be introduced into a host cell by incorporating into the same or different vector and these DNA fragments may be incorporated into chromosome(s) of the host cell.

The present method may be utilized for screening medications having the ability for inhibiting the malignant cell growth in addition to evaluating the potency of a phototrophic herbicide, screening a compound having the hebicidal activity.

When the present method is utilized for evaluating the potency of a phototrophic herbicide or screening a compound having the herbicidal activity, the present method is performed, for example, using PPO genes derived from higher plants such as Arabidopsis, PPO genes derived from algae such as *Chlamydomonas reinhardtii*. As a result, a compound inhibiting the growth of the transformant into which a PPO gene derived from higher plants or algae is introduced is potentially useful as an active ingredient of a herbicide.

Next, a gene which may be used for the present method will be described in detail.

Examples of a rat-derived gene encoding a protein having the PPO activity (hereinafter referred to as "the present rat PPO gene") are (1) a rat-derived gene having about 1.64 kbp of length, for example, a PPO gene encoding a protein having the amino acid sequence shown by SEQ ID: No.1, (2) a gene encoding a protein having the PPO activity and having the amino acid sequence in which one or several amino acids are deleted, substituted, modified or added in the amino acid sequence shown in SEQ ID: No.1. More particularly, for example, mention be made of a PPO gene having the nucleotide sequence shown by SEQ ID: No.2.

Examples of a *Chlamydomonas reinhardtii*-derived gene encoding a protein having the PPO activity (hereinafter referred to as "the present *Chlamydomonas reinhardtii* PPO gene") are (1) a *Chlamydomonas reinhardtii*-derived gene having about 2 kbp of length, for example, a PPO gene encoding a protein having the amino acid sequence shown by SEQ ID: No.9, (2) a gene encoding a protein having the PPO activity and having the amino acid sequence in which one or several amino acids are deleted, substituted, modified or added in the amino acid sequence shown in SEQ ID: No.9. More particularly, for example, mention be made of a PPO gene having the nucleotide sequence shown by SEQ ID: No.10.

The present rat PPO gene is obtained, for example, according to the following method.

RNA is extracted from rat tissues such as liver, kidney and the like according to a method described in Labomanual Genetic Engineering, Suppl. Edition, edited by Matsumura, published by Maruzen K. K., pp76–77, 1990. The extracting procedures may be carried out utilizing a commercially available RNA extracting kit, for example, ISOGEN (Nippon Gene).

The resultant RNA is subjected to the manipulation according to the attached manual using a commercially available poly(A) RNA fractionating kit such as BIOMAG mRNA Purification kit (Perceptive Biosystems) to prepare poly(A) RNA. The resulting poly(A) RNA is subjected to the manipulation according to a method described in Cloning and Sequence: Plant Biotechnology Experimental Manual, edited by Watanabe and Sugiura, published by Nosonbunka Company, pp74–103 (1989) to make cDNA library. This cDNA library making manipulation may utilize a commercially available cDNA library making kit such as ZAP-cDNA Gigapack Cloning Kit (STRATAGENE).

From thus made cDNA library or a commercially available cDNA library such as a rat liver-derived cDNA liver manufactured by STRATAGENE, DNA may be prepared by a method described in Molecular Cloning 2nd edition (authors: J. Sambrook, E. F. Frisch, and T. Maniatis; Cold Spring Harbor Laboratory Press, 1989) 2.60–2.81.

By using thus prepared DNA as a template, a polymerase chain reaction may be performed using an oligonucleotide having the nucleotide sequence shown by SEQ ID: No.3 and that having the nucleotide sequence shown in SEQ ID: No.4 as a primer to amplify a DNA fragment having a partial nucleotide sequence of PPO gene. This amplified DNA fragment having a partial nucleotide sequence of a PPO gene may be cloned into a plasmid using the conventional method described in Labomanual Genetic Engineering, Suppl. Edition, edited by Matsumura, published by Maruzen K. K., pp117–120 (1990) and a commercially available DNA cloning kit such as TA cloning kit (manufactured by Invitrogen) to serve for determining nucleotide sequence. Determination of the nucleotide sequence may be performed by a dideoxy method described, for example, in Molecular Cloning 2nd edition (authors: J. Sambrook, E. F. Frisch and T. Maniatis; Cold Spring Harbor Laboratory Press), 13.42–13.74 (1989). Determination of the nucleotide sequence according to dideoxy method may be performed utilizing a sequencing kit using fluorescently-labeled dideoxynucleotide (more particularly, for example, Dye terminator cycle sequencing kit (manufactured by PE Applied Biosytems) and using a commercially available autosequencer such as DNA Sequencer 373S (manufactured by PE Applied Biosytems).

Thus, the DNA fragment having a partial nucleotide sequence of a rat PPO gene (hereinafter referred to as "the present rat PPO DNA fragment") can be obtained. One example of the present rat PPO DNA fragment is a gene fragment having the nucleotide sequence shown in nucleotide Nos. 639 to 1333 shown by SEQ ID: No.2. The present rat PPO DNA fragment may be utilized in making a PPO gene-specific primer used in a polymerase chain reaction described below or used as a probe for detecting a PPO gene in a hybridization method described below.

Based on the present rat PPO DNA fragment, the present rat PPO gene having entire nucleotide sequence encoding PPO may be obtained according to (1) polymerase chain reaction method or (2) hybridization method.

In order to obtain a PPO gene by utilizing a polymerase chain reaction, a primer having about 15 bp to about 40 bp nucleotide sequence among the nucleotide sequence of the present rat PPO DNA fragment (primer for amplifying 3' downstream region) and about 15 bp to about 40 bp nucleotide sequence among the nucleotide sequence complementary to the base sequence of the present rat PPO DNA fragment (primer for amplifying 5' upstream region) are first prepared. Examples of the primer for amplifying 3' downstream region are a gene fragment having the nucleotide sequence shown in nucleotide Nos.1175 to 1198 by SEQ ID: No.2 and the like, and examples of the primer for amplifying 5' upstream region are a gene fragment having the nucleotide sequence complementary to the nucleotide sequence shown in nucleotide Nos.776 to 799 by SEQ ID: No.2 and the like.

Then, a polymerase chain reaction is performed using as a template a DNA fragment having an adapter DNA added at an end of a rat-derived DNA or a DNA of a vector having rat-derived DNA fragment inserted therein and using a combination of a primer having a partial nucleotide sequence of an adapter DNA or a primer having a partial nucleotide sequence of a vector DNA and a primer for amplifying 5' upstream region and a combination of a primer having a partial nucleotide sequence of an adapter DNA or a primer having a partial nucleotide sequence of a vector DNA and a primer for amplifying 3' downstream region to amplify a DNA fragment containing 5' upstream nucleotide sequence of the present rat PPO DNA fragment and a DNA fragment having 3' downstream nucleotide sequence of the present rat PPO DNA fragment. The DNA fragment having an adapter DNA added at an end of a rat-derived DNA which is used as a template may be prepared by adding as an adapter DNA a polymer of a nucleotide such as cytosine to a rat-derived cDNA prepared above with terminal deoxynucleotidyl transferase or adding a commercially available adapter of a kit for RACE (rapid amplification of cDNA ends) reaction such as an adapter attached to Marathon cDNA amplification kit manufactured by Clontech to a rat-derived cDNA. In addition, one example of the primer having a partial nucleotide sequence of an adapter DNA is a primer specific for an adapter attached to a commercially available RACE (rapid amplification of cDNA ends) reaction kit (for example, AP-1 primer and AP-2 primer attached to Marathon cDNA amplification kit manufactured by Clontech). As the primer having a partial sequence of a vector DNA, when a vector is derived from λ phage, primers specific for an arm region of λ phage such as λ gtII reverse primer and λ gtII forward primer may be used.

Two kinds of thus amplified DNA fragments may be cloned into a plasmid by using the conventional method described in Labomanual Genetic Engineering, Suppl. Edition, edited by Matsumura, published by Maruzen K. K., pp117–120 (1990) or a commercially available DNA cloning kit such as TA cloning kit (manufactured by Invitrogen) to serve for determination of the nucleotide sequence. Determination of the nucleotide sequence may be performed by a dideoxy method described in Molecular Cloning 2nd edition (authors: J. Sambrook, E. F. Frisch and T. Maniatis; Cold Spring Harbor Laboratory Press), 13.42–13.74 (1989). Determination of the nucleotide sequence by a dideoxy method may be performed by utilizing a sequencing kit using a fluorescently labeled dideoxynucleotide such as Dye terminator cycle sequencing kit (manufactured by PE Applied Biosystems) and using a commercially available autosequencer such as DNA Sequencer 373S (manufactured by PE Applied Biosystems). The regions between the thus determined nucleotide sequence and the nucleotide sequence of the present rat PPO DNA fragment which was referenced upon manufacturing the above primer are overlaid to ligate these nucleotide sequences to make one base sequence. Whether or not an entire region of open reading frame encoding PPO is contained in the thus made nucleotide sequence may be studied by investigating open reading frame using a commercially available gene analyzing software such as GENETYX (manufactured by SDC). When a 1.6 kbp or more entire open reading frame is not contained in the determined nucleotide sequence and translation initiation codon or translation termination codon are not contained therein, it is determined that the whole nucleotide sequence of the full length PPO gene is not contained in the nucleotide sequence, and steps for obtaining a gene fragment by a polymerase chain reaction is repeated until PPO gene having the whole nucleotide sequence encoding PPO is obtained. In addition, when open reading frame which is found in the nucleotide sequence determined as described above is missing in either in 5' upstream or 3' downstream side of the determined nucleotide sequence, that is, when a translation initiation codon or translation termination codon is not contained in the open reading frame, steps for obtaining a gene fragment by the polymerase chain reaction same as above may be repeated for obtaining a DNA fragment containing the nucleotide sequence on the missing's side.

Based on the information of the nucleotide sequence thus determined, a primer containing the nucleotide sequence near translation initiation codon in the nucleotide sequence of a PPO gene (N-terminal primer) and a primer containing the nucleotide sequence complementary to the nucleotide sequence near translation termination codon (C-terminal primer) are made, and a polymerase chain reaction may be performed using a rat-derived DNA as a template and using the above both terminal primers to amplify the present rat PPO gene having the entire nucleotide sequence encoding PPO, which may be cloned. Examples of the N-terminal primer include a primer having the nucleotide sequence shown by SEQ ID: No. 5 and a primer having the nucleotide sequence shown by SEQ ID: No. 7, and examples of the C-terminal primer include a primer having the nucleotide sequence shown by SEQ ID: No. 6 and a primer having the nucleotide sequence shown by SEQ ID: No. 8. Alternatively, the DNA fragments obtained by the above steps for obtaining the gene fragment may be ligated with an restriction enzyme recognition site present in the overlapping regions to obtain the present rat PPO gene having the entire nucleotide sequence encoding PPO.

(2) In order to obtain the present rat PPO gene by utilizing a hybridization method, a DNA fragment may be identified by hybridizing a probe of the present rat PPO DNA fragment to a rat-derived DNA and the identified DNA fragment may be isolated.

A probe used for a hybridization method may be prepared by labeling the present rat PPO DNA fragment obtained as described above with a labeling compound by the conventional method described in Molecular Cloning 2nd edition (authors: J. Sambrook, E. F. Frisch and T. Maniatis; Cold Spring Harbor Laboratory Press), 10.6–10.26 (1989). A labeling compound such as a compound containing a radioactive element (hereinafter referred to as "RI") and a fluorescent reagent and the like may be used. Labeling with a compound containing RI may be performed using [α-$^{32}$P] dCTP (manufactured by Amersham) and a random prime labeling kit (manufactured by Boehringer Mannheim) according to the protocol attached to the kit. In addition, non-RI labeling may be performed using DIG-High Prime DNA Labeling and Detection Starter KitI (Boehringer Mannheim) and attached reagents according to the attached protocol.

As a rat-derived DNA for hybridizing with a probe, a rat cDNA library and the like may be used which is obtained by ligating a cDNA derived from a rat to a vector with a suitable adaptor, derived from λ phage and the like and packaging the cDNA into phage particles. Such the gene library may be prepared according to a method, for example, described in Cloning and Sequencing: Plant Biotechnology Experimental Mannual, editted by Watanabe and Sugiura, published by Nosonbunka, pp74–103 (1989). Alternatively, the rat gene libraries sold by Clontech, STRATAGENE and the like may be used.

In order to isolate the present gene, for example, colony hybridization, plaque hybridization and the like to the aforementioned rat gene library may be performed using the probe prepared by the aforementioned method. These may be performed according to a method described in Recombinant DNA Experiment (edited by J. R. Dillon, A. Nasim and E. R. Nestmann, published by Tokyo kagakudozin), pp98–101 (1987) or the conventional method described in Molecular Cloning 2nd edition (authors: J. Sambrook, E. F. Frisch and T. Maniatis; Cold Spring Harbor Laboratory Press), pp1.90–1.104 or 2.108–2.117 (1989). Determination of the nucleotide sequence of the DNA fragment incorporated in the resultant clone may be performed by a dideoxy method described in Molecular Cloning 2nd edition (authors: J. Sambrook, E. F. Frisch and T. Maniatis, Cold Spring Harbor Laboratory Press), pp13.42–13.74 (1989). The determination of the nucleotide sequence by a dideoxy method may be performed by utilizing a sequencing kit using fluorescently labeled dideoxynucleotide such as Dye terminator cycle sequencing kit (manufactured by PE Applied Biosystems) and using a commercially available autosequencer such as DNA Sequencer 373S (manufactured by PE Applied Biosystems). The determined nucleotide sequence may be analyzed using a commercially available gene analyzing software such as GENETYX (SDC) to reveal the entire nucleotide sequence of the present rat PPO gene.

Next, the present *Chlamydomonas reinhardtii*-derived PPO gene is obtained by the following method. The fundamental manipulation may be performed according to the aforementioned description for obtaining the present rat PPO gene.

*Chlamydomonas reinhardtii* is cultured to collect cells and RNA is extracted from the collected cells. A cDNA library is made from the resultant RNA according to a method for obtaining the present rat PPO gene to prepare its DNA.

By using the DNA thus prepared as a template, a polymerase chain reaction may be performed using as a primer an oligonucleotide having the nucleotide sequence shown by SEQ ID: No.11 and that having the nucleotide sequence shown by SEQ ID: No.12 to amplify a DNA fragment having a *Chlamydomonas reinhardtii* PPO gene. The amplified DNA fragment having the nucleotide sequence of PPO gene may be cloned into a plasmid to serve for determination of the nucleotide sequence.

Thus obtained cDNA of the present rat PPO gene or the present rat PPO DNA fragment, or the cDNA of the present *Chlamydomonas reinhardtii* PPO gene may be used to obtain a genome DNA clone of the present rat PPO gene or the present *Chlamydomonas reinhardtii* PPO gene, the nucleotide sequence of which may be determined. First, in the case of the genome DNA clone of the present rat PPO gene, for example, rat tissues such as liver, kidney and the like are taken and a genome DNA is extracted from the taken tissues by manipulations according to a method described in Labomanual Genetic Engineering, Suppl. Edition, edited by Matsumura, published by Maruzen K. K., pp76–77 (1990). On the other hand, in the case of a genome clone of the present *Chlamydomonas reinhardtii* PPO gene, for example, *Chlamydomonas reinhardtii* is cultured to collect cells and a genome DNA is extracted from the collected cells according to the similar procedures. The extracting procedures may be performed using a commercially available DNA extracting kit such as ISOTISSUE (Nippon Gene) according to the protocol attached to the kit to obtain a genome DNA. After the genome DNA is cut with a suitable restriction enzyme, the resultant genome DNA fragment is fractionated according to a NaCl density gradient centrifugation method described in Cloning and Sequencing: Plant Biotechnology Experimental Manual, editted by Watanabe and Sugiura, published by Nosonbunka, pp276–279 (1989). In general, conveniently, a fraction containing a genome DNA fragment having a size suitable for incorporating into a vector, particularly, a fraction containing 9 kbp to 23 kbp genome DNA fragment when a phage vector is used, a fraction containing 30 kbp to 42 kbp genome DNA fragment when a cosmid vector is used is selected from the fractionated respective genome DNA fragments. A genome library is made using the resultant genome DNA fragments and performing the procedures according to a method described in Cloning and Sequencing: Plant Biotechnology Experimental Manual, edited by Watanabe and Sugiura, published by Nosonbunka, pp96–103 and 280–284 (1989) or using a commercially available DNA library making kit such as Lambda EMBL3/Gigapack cloning kit (STRATAGENE) according to the attached protocol. The genome DNA library thus made, or a commercially available genome library such as rat genome library manufactured by STRATAGENE is screened by hybridization using as a probe a cDNA of the present rat PPO gene or the present rat PPO DNA fragment, or a cDNA of the present *Chlamydomonas reinhardtii* PPO gene according to a method described in Cloning and Sequence: Plant Biotechnology Experimental Manual, edited by Watanabe and Sugiura, published by Nosonbunka, pp106–147 (1989) to obtain a genome DNA clone having the nucleotide sequence of the present rat PPO gene, or the present *Chlamydomonas reinhardtii* PPO gene. The resultant genome DNA clone may be subcloned into a suitable vector for analyzing the nucleotide sequence such as a plasmid and the like according to a method described in Cloning and Sequence: Plant Biotechnology Experimental Mannual, edited by Watanabe and Sugiura, published by Nosonbunka, pp152–174 (1989), and sequenced by a dideoxy method and the like according to a primer extension method described in Molecular Cloning 2nd edition (authors; J. Sambrook, E. F. Frisch and T. Maniatis; Cold Spring Harbor Laboratory), pp13.15 (1989). Determination of the nucleotide sequence by dideoxy method may be performed using a commercially available kit such as Dye terminator cycle sequencing kit manufactured by PE Applied Biosystems and using a DNA sequencer such as Model 373S of PE Applied Biosystems.

Further, by a primer extension method described in Bina-Stem Met et al., (1979) Proc. Natl. Acad. Sci.U.S.A.,vol.76, pp731 and Sollner-Webb and R. H. Reeder, (1979) Cell, vol.18, pp485 or a S1 mapping method described in A. J. Berk and P.A.Sharp, (1978) Proc. Natl. Acad. Sci. U.S.A., vol.75, pp1274 and the like, each transcription initial point of the genome DNA of the present rat PPO gene or the present *Chlamydomonas reinhardtii* PPO gene may be decided. At about 1 kb to about 10 kb upstream from this transcription initiation point, there is a promoter sequence responsible for controlling the gene expression.

In addition, the present rat PPO gene and the present *Chlamydomonas reinhardtii* PPO gene can be utilized as a means for obtaining or generating a gene resistance to a PPO activity inhibiting agent known as a phototrophic herbicide. For example, it becomes possible to generate a new herbicide-resistant gene by introducing into a PPO gene a mutation which gives a change to the amino acid sequence of PPO encoded by the present rat PPO gene or the present *Chlamydomonas reinhardtii* PPO gene and screening a gene encoding the amino acid sequence of PPO showing phototrophic herbicide-resistance. More particularly, it becomes possible to generate a new phototrophic herbicide-resistant gene by inducing a random mutation in the nucleotide sequence of the present rat PPO gene or the present *Chlamydomonas reinhardtii* PPO gene to introduce a mutation into the amino acid sequence according to a method described in A. Greener, M. Callahan, Strategies, 1994, Vol.7, pp32 to 34, and the like. In addition, it also becomes possible to generate a new phototrophic herbicide-resistant gene by introducing a site-specific mutation into the nucleotide sequence of the present rat PPO gene or the present *Chlamydomonas reinhardtii* PPO gene to alter the amino acid sequence according to a gapped duplex method described in W. Kramer, et al., Nucleic Acids Research, 1984, vol.12, pp9441 or W. Kramer, H. J. Frits, Methods in Enzymology, 1987, vol.154, pp350, or a Kunkel method described in T. A. Kunkel, Proc. of Natl. Acad. Sci. U.S.A., 1985, vol.82, pp488 or T. A. Kunkel, et. al., Methods in Enzymology, 1987, vol. 154, pp367, and the like. Further, it also becomes possible to generate a new phototrophic herbicide-resistant gene by making a gene encoding a chimera protein in which one or several partial amino acid sequences among the amino acid sequence of PPO encoded by the present rat PPO gene or the present *Chlamydomonas reinhardtii* PPO gene are substituted with a part of the amino acid sequence of the present *Chlamydomonas reinhardtii* PPO gene, the present rat PPO gene or PPO gene derived from other organisms. The effects of the thus made phototrophic herbicide-resistant gene (expresasion of herbicide resistance) can be effectively confirmed by, for example, introducing a generated herbicide-resistant gene into a microorganism defective in PPO or a microorganism having PPO sensitive to a subject herbicide, selecting a transformed microorganism, and treating the transformed microorganism with the subject herbicide to reselect a herbicide-resistant colony.

As a vector which comprises the present rat PPO gene or the present *Chlamydomonas reinhardtii* PPO gene, mention may be made of a plasmid made by cloning into pCR2.1 (Invitrogen) a PPO gene having the nucleotide sequence encoding the amino acid sequence shown by SEQ ID: No.1 or No.9 and the plasmid has the such the characteristics that a vector part is small and a copy number is large in *Escherichia coli* and, thus, is suitable for preparing DNA or analyzing the DNA structure.

A vector which can cause the present rat PPO gene or the present *Chlamydomonas reinhardtii* PPO gene to be expressed in a host cell can be constructed by, for example, inserting into a vector a DNA fragment in which (1) a promoter functionable in a host cell, and (2) the present rat PPO gene or the present *Chlamydomonas reinhardtii* PPO gene and, if necessary, (3) a terminator functionable in a host cell are operatively linked in an operative manner in the above order. As used herein, "operatively" means that the present rat PPO gene or the present *Chlamydomonas reinhardtii* PPO gene are ligated to a promoter (and, if necessary, a terminator) so that they are expressed under the control of the promoter (and the terminator) upon introduction of the vector into the host cell to transform the host cell.

As a "a promoter functionable in a host cell" is not limited to specified ones but may be any promoters having the transcriptional activity in a host cell to be transformed. For example, mention may be made of *Escherichia coli* lactose operon promoter, yeast alcohol dehydrogenase gene (ADH) promoter, adenovirus major late (Ad.ML) promoter, SV40 early promoter, baculovirus promoter, nopaline synthase gene (NOS) promoter, octopine synthase gene (OCT) promoter, cauliflower mosaic virus (CaMV)-derived 19S and 35S promoters, phenylalanine ammonia lyase (PAL) gene promoter, chalcone synthase (CHS) gene promoter and the like.

"A terminator functionable in a host cell" is not limited to specified ones but may be any terminators having the transcription terminating activity in a host cell to be transformed. For example, mention may be made of *Escherichia coli* lactose operon terminator, yeast HIS terminator, ADH1 terminator, SV40 early splicing region, nopaline synthase gene (NOS) terminator, garlic virus GV1, GV2 terminators and the like.

A host cell can be transformed by introducing the above vector into the host cell. For example, when a host cell is a microorganism, the above vector can be introduced into a cell of the microorganism by the known means such as a calcium chloride method, an electroporation method (Methods in Electroporation: Gene Pulser/E. coli Pulser System, Bio-Rad Laboratories, 1993) and the like. On the other hand, when a host cell is a plant, a transformed plant cell can be obtained by introducing the above present vector into a cell of the plant by the known means such as an Agrobacterium infection method (JP-B-2-58917 (examined) and JP-A-60-70080 (laid-opened)), an electroporation to a protoplast method (JP-A-60-251887 (laid-opened) and JP-A-5-68575 (laid-opened)), or a particle gun method (JP-A-5-508316 (laid-opened) and JP-A-63-258525 (laid-opened)) to select a cell into which the present rat PPO gene or the present *Chlamydomonas reinhardtii* PPO gene is introduced. From the resultant transformed plant cell, a transformed plant body can be obtained by regenerating a transformed plant by a plant cell culturing method described in, for example, Plant Genetic Manipulation Manual: A method for generating A Transgenic Plant (author: Uchimiya, Kodansha Scientific, 1990, pp.27 to 55).

Furthermore, PPO activity of a host cell or sensitivity of a host cell to the inhibitor for PPO activity may be altered by transforming a host cell by introducing into the host cell a vector containing a DNA fragment in which (1) a promoter functionable in a host cell and (2) the present rat PPO gene or the present *Chlamydomonas reinhardtii* PPO gene and, if necessary, (3) a terminator functionable in a host cell using the present rat PPO gene or the present *Chlamydomonas reinhardtii* PPO gene.

As used herein, "a promoter functionable in a host cell" is not limited to specific ones but may be any promoters having the transcriptional activity in a host cell to be transformed. For example, mention may be made of *Escherichia coli* lactose operon promoter, yeast alcohol dehydrogenase gene (ADH) promoter, adenovirus major late (Ad.ML) promoter, SV40 early promoter, baculovirus promoter, nopaline synthase gene (NOS) promoter, octopine synthase gene (OCT) promoter, cauliflower mosaic virus (CaMV)-derived 19S and 35S promoters, phenylalanine ammonia lyase (PAL) gene promoter, chalcone synthase (CHS) gene promoter and the like.

"A terminator functionable in a host cell" is not limited to specified ones but may be any terminators having the transcription terminating activity in a host cell to be transformed. For example, mention may be made of *Escherichia coli* lactose operon terminator, yeast HIS terminator, ADH1 terminator, SV40 early splicing region, nopaline synthase gene (NOS) terminator, garlic virus GV1, GV2 terminators and the like.

By the above method for altering a host cell, for example, a resistance to a phototrophic herbicide targeting PPO can be imparted to a plant.

Other PPO genes can be obtained and utilized by the aforementioned method for obtaining the present rat PPO gene. For example, in order to obtain a rabbit-derived PPO gene, a commercially available rabbit cDNA library, primers, etc shown by SEQ ID: No.3 and No.4 and the like may be used.

EXAMPLES

The following Examples illustrate the present invention in detail but do not limit the present invention.

Example 1
(Cloning of a Rat PPO DNA Fragment)

An oligonucleotide having the nucleotide sequence shown by SEQ ID: No.3 and that having the nucleotide sequence shown by SEQ ID: No.4 were prepared. The oligonucleotides were synthesized using a DNA synthesizer (PE Applied Systems: Model 394 DNA/RNA Synthesizer), and using as a solvent for synthesis a solvent for Model 394 DNA/RNA Synthesizer (PE Applied Systems) and using as a DNA synthesis reagent phosphoamidite reagents (PE Applied Systems) corresponding to adenine, cytosine, guanine and thymine. The synthesized oligonucleotides were purified by an oligonucleotide purifying cartridge (PE Applied Systems: OPC cartridge) and dried under reduced pressure to prepare oligonucleotides.

A library comprising λ ZAPII vector having inserted cDNA derived from a rat liver (manufactured by STRATAGENE) (hereinafter referred to as "rat cDNA library") was spread over several plates in NZCYM agar medium to amplify according to a method described in Molecular Cloning $2^{nd}$ edition (authors: J. Sambrook, E. F. Frisch, T. Maniatis; Cold Spring Harbor Laboratory Press, 1989), 2.60–2.65 and phage particles were eluted with an SM buffer from the agar medium per each plate (hereinafter referred to as "amplified library"). A DNA was extracted from the amplified library using a DNA extracting kit (Lambda-TRAP PLUS: manufactured by Clontech) to prepare a phage cloned DNA. A polymerase chain reaction was performed using this phage cloned DNA as a template to amplify the DNA fragment. A reaction solution for polymerase chain reaction was prepared by taking 10 pmol of an oligonucleotide having the nucleotide sequence shown by SEQ ID: No. 3, 10 pmol of an oligonucleotide having the nucleotide sequence shown by SEQ ID: No. 4, 5 μl 10×PCR buffer (manufactured by TAKARA SHUZO CO., LTD), 0.25 μl Taq DNA polymerase (TaKaRa Taq manufactured by TAKARA SHUZO CO., LTD), each 10 nmol of four kinds of nucleotides (dATP, dCTP, dGTP, dTTP: manufactured by TAKARA SHUZO CO., LTD), and 10 ng of the phage clone DNA in a 0.5 ml volume of a polymerase chain reaction tube and adding sterile distilled water to total 50 μl. Each step of polymerase chain reaction was carried out under the following conditions: The first cycle comprising a denaturing step holding a temperature at 95° C. for 1 minute, an annealing step holding a temperature at 55° C. for 2 minutes, and an extension step with a DNA polymerase holding a temperature at 72° C. for 3 minutes was performed once, and the second cycle comprising a denaturing step holding a temperature at 95° C. for 1 minute, an annealing step holding a temperature at 55° C. for 1.5 minutes, and an extentsion step with a polymerase holding a temperature at 72° C. for 2 minutes was performed 34 times. After completion of the polymerase chain reaction, the reaction solution was analyzed on an agarose gel electrophoresis to select an amplified library from which about 700 bp amplified DNA fragment is detected. the nucleotide sequence shown by SEQ ID: No.3, 10 pmol of an oligonucleotide having the nucleotide sequence shown by SEQ ID: No. 4, 5, μl 10×PCR buffer (manufactured by TAKARA SHUZO CO., LTD), 0.25, μl TaKaRa Taq (manufactured by TAKARA SHUZO CO., LTD), each 10 nmol of four kinds of nucleotides (dATP, dCTP, dGTP, dTTP: manufactured by TAKARA SHUZO CO., LTD), and 10 ng of the phage clone DNA in a 0.5 ml volume of a polymerase chain reaction tube and adding sterile distilled water to total 50 μl. Each step of polymerase chain reaction was carried out under the following conditions: The first cycle comprising a denaturing step holding a temperature at 95° C. for 1 minute, an annealing step holding a temperature at 55° C. for 2 minutes, and an extension step with a DNA polymerase holding a temperature at 72° C. for 3 minutes was performed once, and the second cycle comprising a denaturing step holding a temperature at 95° C. for 1 minute, an annealing step holding a temperature at 55° C. for 1.5 minutes, and an extension step with a polymerase holding a temperature at 72° C. for 2 minutes was performed 34 times. After completion of the polymerase chain reaction, the reaction solution was analyzed on an agarose gel electrophoresis to select an amplified library from which about 700 bp amplified DNA fragment is detected.

Next, *Escherichia coli* was infected with the selected amplified library and pBluescript vector containing a rat cDNA was prepared according to the description of manual attached to the above rat cDNA library, which was transformed into *Escherichia coli* to make an *Escherichia coli* library. Then, this *Escherichia coli* library was used to make a membrane for hybridization according to a method described in Recombinant DNA Experiment (editted by J. R. Dillon, A Nasim, E. R. Nestmann, Tokyo Kagakudozin, 1987), pp98 to 100. Further, this membrane was used to perform hybridization using DIG-High Prime DNA Labeling and Detection Starter Kit I (manufactured by Boehringer Mannheim) and reagents attached thereto and according to the protocol attached thereto. As a probe, a DNA fragment having the nucleotide sequence shown by nucleotide Nos. 639 to 1333 in SEQ ID; No. 2. As a result, two clones which strongly hybridize with the probes were obtained.

The nucleotide sequence of the DNA fragment harbored by the resultant clone was determined using Dye terminator cycle sequencing kit (manufactured by PE Applied Systems) and a DNA sequencer 373S (manufactured by PE Applied Systems). As a result, the nucleotide sequence shown by nucleotide Nos.270 to 1636 in SEQ ID: No. 2 was revealed and it was found that the resultant two clones harbor the DNA fragments having the same nucleotide sequence. In addition, since a translation initiation codon is missing in the determined base sequence, a PPO gene encoded in the cloned DNA fragment was found to lack a 5' upstream region containing a translation initiation codon.

Example 2
(Cloning of a Full Length PPO Gene)

In order to clone a 5' upstream region of a PPO gene which is missing in the PPO DNA fragment obtained in Example 1, a polymerase chain reaction was performed using as a template a DNA extracted from a rat cDNA library to amplify the DNA fragment. A reaction solution for polymerase chain reaction was prepared by taking 10 pmol of an oligobase having the nucleotide sequence shown by SEQ ID: No. 4, 10 pmol T3 primer (manufactured by TAKARA SHUZO CO., LTD), 0.5 µl long amplifying Taq DNA polymerase (TaKaRa LA Taq manufactured by TAKARA SHUZO CO., LTD), 5 µl 10×LA PCR buffer (manufactured by TAKARA SHUZO CO., LTD), each 20 nmol of four kinds of nucleotides (dATP, dCTP, dGTP, dTTP: manufactured by Clontech), and 10 ng of phage cloned DNA in 0.5 ml volume of a polymerase chain reaction tube and adding sterile distilled water to total 50 µl. Each step of polymerase chain reaction was carried out under the following conditions: The first cycle comprising a denaturing step holding a temperature at 95° C. for 1 minute, an annealing step holding a temperature at 55° C. for 2 minutes, and an extension step with a DNA polymerase holding a temperature at 72° C. for 3 minutes was performed once, and the second cycle comprising a denaturing step holding a temperature at 95° C. for 1 minute, an annealing step holding a temperature at 55° C. for 1.5 minutes, and an extension step with a polymerase holding a temperature at 72° C. for 2 minutes was performed 34 times. After completion of the polymerase chain reaction, the reaction solution was filtered by a spin column (MicroSpin S-400HR manufactured by Pharmacia Biotech) to purify the DNA fragments amplified by the polymerase chain reaction. (manufactured by TAKARA SHUZO CO., LTD), 5 µl 10×LA PCR buffer (manufactured by TAKARA SHUZO CO., LTD), each 20 nmol of four kinds of nucleotides (dATP, dCTP, dGTP, dTTP: manufactured by Clontech), and 10 ng of phage cloned DNA in a 0.5 ml volume of a polymerase chain reaction tube and adding sterile distilled water to total 50 µl. Each step of polymerase chain reaction was carried out under the following conditions: The first cycle comprising a denaturing step holding a temperature at 95° C. for 1 minute, an annealing step holding a temperature at 55° C. for 2 minutes, and an extension step with a DNA polymerase holding a temperature at 72° C. for 3 minutes was performed once, and the second cycle comprising a denaturing step holding a temperature at 95° C. for 1 minute, an annealing step holding a temperature at 55° C. for 1.5 minutes, and an extension step with a polymerase holding a temperature at 72° C. for 2 minutes was performed 34 times. After completion of the polymerase chain reaction, the reaction solution was filtered by MicroSpin S-400HR (manufactured by Pharmacia Biotech) to purify the DNA fragments amplified by the polymerase chain reaction.

Next, 2 µl of the purified solution of the DNA fragment amplified by the above polymerase chain reaction, 50 ng of linearized pCR2.1 (manufactured by Invitrogen), 1 µl of Ligation buffer (manufactured by Invitrogen), and 4 Weiss units of T4 DNA Ligase (manufactured by Invitrogen) were taken into 1.5 ml microtube, a sterile distilled water was added thereto to total 10 µl to mix, a DNA ligation reaction was performed by holding a temperature at 14° C. for 16 hours to ligate the DNA fragment amplified by the polymerase chain reaction to pCR2.1. After completion of ligation reaction, a competent cell of *Escherichia coli* strain INV α F(manufactured by Invitrogen) was transformed with 1 µl of the reaction solution to select a strain which became ampicillin-resistant. Further, plasmid DNA was extracted from the selected strain and they were cut with restriction enzymes and analyzed on an agarose electrophoresis to select a plasmid in which about 1.4 kbp DNA fragment amplified by polymerase chain reaction was cloned.

The nucleotide sequence of the DNA fragment harbored by the selected plasmid was determined using Dye terminator cycle sequencing kit (PE Applied Bio Systems) and a DNA sequencer 373S (manufactured by PE Applied Bio Systems). The determined nucleotide sequence was analyzed and found that the cloned 1.4 kbp DNA fragment overlap with the DNA fragment obtained in Example 1 by about 1.1 kbp and contain about 150 bp upstream from translation initiation point.

The above plasmid having about 1.4 kbp DNA fragment was cut with a restriction enzyme, EcoRI and HincII (both manufactured by TAKARA SHUZO CO., LTD) to recover about 550 bp fragment. On the other hand, the plasmid harbored by the clone obtained in Example 1 was cut with a restriction enzyme, EcoRI and HincII (both manufactured by TAKARA SHUZO CO., LTD) and its 5' terminal was dephosphorylated with calf intestine alkaline phosphatase (manufactured by TAKARA SHUZO CO., LTD).

The aforementioned two DNA fragments were taken in a microtube, and ligated using a DNA ligation kit (manufactured by TAKARA SHUZO CO., LTD). *Escherichia coli* HB101 competent cell (manufactured by TAKARA SHUZO CO., LTD) was transformed with the resultant reaction solution and selected a strain which became ampicillin-resistant. The plasmid harbored by the selected strain was cut with restriction enzymes EcoRI and XhoI (both manufactured by TAKARA SHUZO CO., LTD), and analyzed on an agarose gel electrophoresis to select a plasmid into which about 1.7 kbp DNA fragment is cloned.

The nucleotide sequence of the DNA fragment harbored by the resultant clone was determined using Dye terminator cycle sequencing kit (manufactured by PE Applied Bio Systems) and a DNA sequencer 373S (manufactured by PE Applied Bio Systems). As a result, the nucleotide sequence shown by SEQ ID: No.2 was revealed and the cloned DNA fragment was found to contain a full length structural gene (1431 bp) encoding a rat-derived PPO.

Example 3
(Analysis of PPO Amino Acid Sequence)

The nucleotide sequence of the rat-derived PPO gene cDNA determined in Example 2 was analyzed to translate the amino acid sequence using genetic analyzing software (GENETYX: manufactured by SDC). As a result, a protein encoded by the cloned rat-derived PPO gene cDNA was found to be composed of 477 amino acid residues and its amino acid sequence was that shown by SEQ ID: No. 1.

Example 4
(Construction of a Vector for Expressing a Rat PPO Gene in *Escherichia coli*)

An oligonucleotide having the nucleotide sequence shown by SEQ ID: No. 5 and that having the nucleotide sequence shown by SEQ ID: No. 6 were prepared. The oligonucleotides were synthesized using a DNA synthesizer (PE Applied Systems: Model 394 DNA/RNA Synthesizer) and using a solvent for Model 394 DNA/RNA Synthesizer as a solvent (PE Applied Systems) and using as a DNA synthesizing reagent phosphoamidite reagents corresponding to adenine, cyctosine, guanine and thymidine (PE Applied Systems). The synthesized oligonucleotides were purified by an oligonucleotide purifying cartridge (PE Applied Systems: OPC cartridge) and dried under reduced pressure to prepare oligonucleotides.

A polymerase chain reaction was performed using as a template a full length gene cDNA encoding the rat-derived PPO obtained in Example 2 and as a primer an oligonucleotide having the nucleotide sequence shown by SEQ ID: No. 5 and that having the nucleotide sequence shown by SEQ ID: No. 6 to amplify the about 1.5 kbp DNA fragment encoding PPO. A reaction solution in the polymerase chain reaction was prepared by taking 10 pmol of an oligonucleotide having the nucleotide sequence shown by SEQ ID; No. 5, 10 pmol of an oligonucleotide having the nucleotide sequence shown by SEQ ID: No. 6, 0.5 µl of long-amplifying Taq DNA polymerase (TaKaRa LA Taq manufactured by TAKARA SHUZO CO., LTD.), 5.0 µl 10×LA PCR buffer (manufactured by TAKARA SHUZO CO., LTD), each 20 nmol of four kinds of nucleotides (dATP, dCTP, dGTP and dTTP; manufactured by Clontech), and 10 ng of a plasmid containing full length cDNA of the rat PPO obtained in Example 2 in a 0.5 ml volume of a polymerase chain reaction tube and adding sterile distilled water to total 50 µl. Each step in the polymerase chain reaction was performed under the following conditions: The first cycle comprising a denaturing step holding a temperature at 95° C. for 1 minute, an annealing step holding a temperature at 55° C. for two minutes, and extension step with a DNA polymerase holding a temperature at 72° C. for three minutes was performed once, and the second cycle comprising a denaturing step holding a temperature at 95° C. for 1 minute, an annealing step holding a temperature at 55° C. for 1.5 minutes, and an extension step holding a temperature at 72° C. for 2 minutes was performed 34 times.

After the polymerase chain reaction, the DNA fragment amplified by the polymerase chain reaction was purified by filtering the reaction solution with a spin column (MicroSpin S-400HR manufactured by Pharmacia Biotech). A terminus of this DNA fragment was cut with restriction enzymes SacII and SmaI. On the other hand, pBluescript II SK+ (manufactured by Stratagene) was cut with restriction enzymes SacII and SmaI (both manufactured by TAKARA SHUZO CO., LTD) and the 5' end was dephosphorylated with calf intestine alkaline phosphatase (manufactured by TAKARA SHUZO CO., LTD).

The aforementioned two DNA fragments were taken in a microtube, and ligated using a DNA ligation kit (manufactured by TAKARA SHUZO CO., LTD). A competent cell of *Escherichia coli* JM109 (manufactured by TAKARA SHUZO CO., LTD) was transformed with the resultant reaction solution to select a strain which became ampicillin-resistant and a plasmid DNA was prepared from the ampicillin-resistant strain to obtain a vector for expressing rat PPO gene in *Escherichia coli*.

Example 5
(Complementation Experiment of *Escherichia coli* hemG-deficient Strain with Rat PPO Gene)

The expression vector obtained in Example 4 was introduced into *Escherichia coli* PPO gene (hemG locus)-deficient mutant strain BT3, which was spread-inoculated on LB agar medium containing kanamycin at final concentration of 10 µg/ml and ampicillin at final concentration of 50 µg/ml to culture at 37° C. for 2 days. BT3 strain became less proliferative and formed only small colonies, while a strain having the introduced vector for expressing rat PPO gene formed relatively large colonies on the LB plate.

Example 6
(Test on the Ability of a Compound to Inhibit the Rat PPO Activity)

An overnight cultured bacterial solution of *Escherichia coli* strain BT3 into which a introduced vector for expressing the rat PPO gene obtained in Example 5 is diluted to turbidity($OD_{600}$) of 1.0. 0.05% medium volume equivalent amount of this diluted bacterial solution is inoculated on YPT liquid medium containing no various test compounds and also is inoculated on YPT liquid medium containing various compounds at a variety of concentrations to culture by shaking at 37° C. and turbidity ($OD_{600}$) 16 hours after culturing is measured. The concentration at which 50% growth inhibition by various test compounds is seen is calculated by adopting turbidity of the system having no addtion of test compound as 100%. By comparing the concentrations in various test compounds, the PPO inhibiting abilities of test compounds are determined.

Example 7
(Obtaining of *Escherichia coli* for Expressing Rat PPO Gene, into which lac Repressor Gene is Introduced)

pBR322 was cut with restriction enzymes HindIII and AvaI (both manufactured by TAKARA SHUZO CO., LTD) to recover the about 1.4 kb fragment. Separately, pREP4 was cut with restriction enzymes HindIII and AvaI (both manufactured by TAKARA SHUZO CO., LTD) to recover the about 2.4 kb fragment and its 5'end was dephosphorylated with calf intestine alkaline phosphatase (manufactured by TAKARA SHUZO CO., LTD).

The aforementioned two DNA fragments were taken in a microtube and ligated using a DNA ligation kit (manufactured by TAKARA SHUZO CO., LTD). A competent cell (manufactured by TAKARA SHUZO CO., LTD) of *Escherichia coli* strain JM109 was transformed with the resultant reaction solution to select a strain which became kanamycin and tetracyclin-resistant and a plasmid DNA was prepared from the kanamycin and tetracyclin-resistant strain to obtain a vector for expressing lac repressor. The vector was introduced into *Escherichia coli* strain BT3 to select a strain which became kanamycin , tetracyclin and ampicillin-resistant. Further, the expression vector obtained in Example 4 was introduced into the tetracyclin-resistant strain to select a strain which became kanamycin and tetracyclin- and ampicillin-resistant to obtain *Escherichia coli* strain BT3 into which the rat PPO gene and lac repressor gene were introduced.

Example 8
(Assaying of the Ability of a Compound to Inhibit the PPO Activity Using *Escherichia coli* Strain BT3 for Expressing Rat PPO Gene, into which lac Repressor is Introduced)

An overnight cultured bacterial solution of *Escherichia coli* strain BT3 for expressing a rat PPO gene, into which lac repressor was introduced, obtained in Example 7 was diluted to turbidity ($OD_{600}$) of 0.5. 0.1% medium volume equivalent amount of this diluted bacterial solution was inoculated on YPT liquid medium containing no test compound and also was inoculated on YPT liquid medium containing various test compounds at various concentrations to culture by shaking at 37° C. and turbidity ($OD_{600}$) 20 hours after culturing was measured. The concentration at which 50% growth inhibition by a compound having the structure shown in FIG. 4 was seen was calculated and found to be 0.11 ppm under the condition that the growth rate of the transformant is 100% in the system of no addition of test compound.

Example 9
(Cloning of *Chlamydomonas reinhardtii* PPO DNA Fragment)

*Chlamydomonas reinhardtii* strain CC407 was obtained from Chlamydomonas Genetics Center (address: DCMB Group, Department of Botany, Box 91000, Duke University, Durham, N.C. 27708-1000, USA), and cultured in TAP liquid medium comprising 7 mM $NH_4Cl$, 0.4 mM $MgSO_4.7H_2O$, 0.34 mM $CaCl_2$, 25 mM potassium calcium, 0.5 mM Tris (pH 7.5), 1 ml/L Hutner trace elements, and 1 ml/L glacial acetic acid (E. H. Harris, The Chlamydomonas Sourcebook, Academic Press, San Diego, 1989, pp576–577) under the light (200 $\mu E/m^2/s^1$) for 5 days to obtain 200 ml of culture containing cells at early stationary proliferation stage ($1.0 \times 10^6$ cells/ml).

The whole RNA was prepared from the cells by performing the manipulation using ISOGEN (Nippon gene) according to the attached manual. Further, poly(A) RNA was fractionated using BioMag mRNA Purification Kit (Perceptive Biosystems) by performing the manipulation according to the attached manual. From the resultant poly (A)RNA, a cDNA was synthesized using Marathon cDNA Amplification Kit (Clontech) by performing the manipulation according to the attached manual and this was used as a template for polymerase chain reaction.

An oligonucleotide having the nucleotide sequence shown by SEQ ID: No. 11 and that having the nucleotide sequence shown by SEQ ID: 12 were prepared as a primer for polymerase chain reaction. The oligonucleotides were synthesized using a DNA synthesizer (PE Applied Systems: Model 394 DNA/RNA Synthesizer) and using as a solvent for synthesis a solvent for Model 394 DNA/RNA Synthesizer (PE Applied Systems) and using as a reagent for synthesizing DNA phosphoamidite reagents corresponding to adenine, cytosine, guanine and thymine (PE Applied Systems). Synthesized oligonucleotides were purified with oligonucleotide purifying cartridge (PE Applied Systems: OPC cartridge) and dried under reduced pressure to prepare an oligonucleotide.

A polymerase chain reaction was performed by preparing a reaction solution using Advantage cDNA PCR kit (Clontech) according to the attached manual and repeating once a cycle comprising 94° C. for 1 minute and 70° C. for 4 minutes, four times a cycle comprising 94° C. for 10 seconds, then 70° C. for 4 minutes, five times a cycle comprising 94° C. for 10 seconds, then 68° C. for 4 minutes, and 25 times a cycle comprising 94° C. for 10 seconds, then 65° C. for 5 minutes, and an aliquot of the reaction solution was subjected to agarose gel electrophoresis to confirm that about 2 kbp amplified fragment is obtained. Further, the excess primers in the reaction solution were removed by performing the manipulation using a spin column (MicroSpin S400HR Pharmacia Biotech) according to the attached manual and the manipulation was performed using TA Cloning Kit (Invitrogen) according to the attached manual to clone the amplified fragment into pCR2.1 plasmid.

The nucleotide sequence of the DNA fragment harbored by the resultant recombined plasmid was determined using Dye terminator cycle sequencing kit (manufactured by PE Applied Bio Systems) and a DNA sequencer 373S (manufactured by PE Applied Bio Systems). As a result, the nucleotide sequence shown by SEQ ID; No. 10 was revealed and it was found to be full length cDNA encoding the amino acid sequence shown by SEQ ID: No. 9 by the analysis using Genetic Analyzing software GENETYX (SDC).

Example 10
(Construction of a Vector for Expressing a *Chlamydomonas reinhardtii* PPO Gene in *Escherichia coli*)

An oligonucleotide having the nucleotide sequence shown by SEQ ID: No. 13, in which a restriction enzyme SacI recognition sequence is introduced at an end, and an oligonucleotide having the nucleotide sequence shown by SEQ ID: No. 14, in which a restriction enzyme SalI recognition sequence is introduced at an end were prepared. The oligonucleotides were synthesized using a DNA synthesizer (PE Applied Systems: Model 394 DNA/RNA Synthesizer) and as a solvent for synthesis a solvent for Model 394 DNA/RNA Synthesizer (PE Applied Systems) and using as a reagent for DNA synthesis a phosphoamidite reagent corresponding to adenine, cytosine, guanine, and thymine (PE Applied Systems). The synthesized oligonucleotides were purified by an oligonucleotide purifying cartridge (PE Applied Systems: OPC cartridge) and dried under reduced pressure to prepare an oligonucleotide.

A polymerase chain reaction was performed using as a template a full length gene cDNA encoding PPO derived from *Chlamydomonas reinhardtii* obtained in Example 9 and as a primer an oligonucleotide having the nucleotide sequence shown by SEQ ID: No. 13 and that having the nucleotide sequence shown by SEQ ID: No 14 to amplify the about 2 kbp DNA fragment encoding PPO. A reaction solution in the polymerase chian reaction was prepared by taking 10 pmol of an oligonucleotide having the nucleotide sequence shown by SEQ ID: No. 13, 10 pmol of an oligonucleotide having the nucleotide sequence shown by SEQ ID: No. 14, 0.5 μl of long-amplifying Taq DNA polymerase (TaKaRa LA Taq manufactured by TAKARA SHUZO CO., LTD), 5.0 μl of 10×LA PCR buffer (manufactured by TAKARA SHUZO CO., LTD), each 20 nmol of four kinds of nucleotides (dATP, dCTP, dGTP, dTTP: manufactured by Clontech), 10 ng of a plasmid containing full length cDNA of *Chlamydomonas reinhardtii* PPO obtained in Example 9 in 0.5 ml volume of a polymerase chain reaction tube and adding sterile distilled water to total 50 μl. Each step in the polymerase chain reaction was performed under the following conditions: After the first cycle comprising a denaturing step holding a temperature at 95° C. for 1 minute, an annealing step holding a temperature at 55° C. for 2 minutes, and an extension step with a DNA polymerase holding a temperature 72° C. for 3 minutes was performed once, the second cycle comprising a denaturing step holding a temperature at 95° C. for 1 minute, an annealing step holding a temperature at 55° C. for 15 minutes, and an extension step holding a temperature at 72° C. for 2 minutes was performed 34 times. (manufactured by TAKARA SHUZO CO., LTD), 5.0 µl of 10×LA PCR buffer (manufactured by TAKARA SHUZO CO., LTD), each 20 nmol of four kinds of nucleotides (dATP, dCTP, dGTP, dTTP: manufactured by: Clontech), 10 ng of a plasmid containing full length cDNA of *Chlamydomonas reinhardtii* PPO obtained in Example 9 in 0.5 ml volume of a polymerase chain reaction tube and adding sterile distilled water to total 50 µl. Each step in the polymerase chain reaction was performed under the following conditions; After the first cycle comprising a denaturing step holding a temperature at 95° C. for 1 minute, an annealing step holding a temperature at 55° C. for 2 minutes, and an extension step with a DNA polymerase holding a temperature at 72° C. for 3 minutes was performed once, the second cycle comprising a denaturing step holding a temperature at 95° C. for 1 minute, an annealing step holding a temperature at 55° C. for 15 minutes, and an extension step holding a temperature at 72° C. for 2 minutes was performed 34 times.

After the polymerase chain reaction, the DNA fragment amplified by the polymerase chain reaction was purified by filtering the reaction solution with MicroSpin S-400HR (manufactured by Pharmacia Biotech). The end of this DNA fragment was cut with restriction enzymes SacI and SalI. On the other hand, the plasmid pUC118 (manufactured by TAKARA SHUZO CO., LTD) was cut with restriction enzymes SacI and SalI (both manufactured by TAKARA SHUZO CO., LTD) and 5'end was dephosphorylated with calf intestine alkaline phosphatase (manufactured by TAKARA SHUZO CO., LTD).

The aforementioned two DNA fragments were taken in a microtube and ligated using a DNA ligation kit (manufactured by TAKARA SHUZO CO., LTD). A competent cell (manufactured by TAKARA SHUZO CO., LTD) of *Escherichia coli* JM109 was transformed with the resultant reaction solution to select a strain which became ampicillin-resistant and a plasmid DNA was prepared from the ampicillin-resistant strain to obtain a vector for expressing *Chlamydomonas reinhardtii* PPO gene.

Example 11
(Complementation Experiment of *Escherichia coli* hemG-deficient Strain with *Chlamydomonas reinhardtii* PPO Gene)

The expression vector obtained in Example 10 was introduced into PPO gene (hemG locus)-deficient mutant *Escherichia coli* strain BT3 described in F. Yamamoto, H. Inokuchi, H. Ozeki, (1988) Japanese Journal of Genetics, vol.63, pp237 to 249, which was spread-inoculated on LB agar medium containing kanamycin to the final concentration of 10 µg/ml and ampicillin to the final concentration of 50 µg/ml to culture at 37° C. for 2 days. *Escherichia coli* BT3 strain became less proliferative and formed small colonies, while a strain having introduced vector for expressing *Chlamydomonas reinhardtii* PPO gene formed relatively large colonies on the LB plate.

Example 12
(Construction of a PPO Gene Expressing Vector for Direct Introduction)

In order to express a rat-derived PPO gene in a plant cell, a PPO gene expressing vector for directly introducing a plant is constructed.

An oligonucleotide having the nucleotide sequence shown by SEQ ID: No. 7 and that having the nucleotide sequence shown by SEQ ID: No.8 are prepared. The oligonucleotides are synthesized using a DNA synthesizer (PE Applied Systems: Model 394 DNA/RNA Synthesizer) and using as a solvent for DNA synthesis a solvent for Model 394 DMA/RNA Synthesizer (PE Applied Systems) and as a reagent for synthesis phosphoramidite reagents corresponding to adenine, cytosine, guanine and thymine (PE Applied Systems). The synthesized oligonucleotides are purified by an oligonucleotide purifying cartridge (PE Applied Systems: OPC cartridge) and dried under reduced pressure to prepare an oligonucleotide.

A polymerase chain reaction is performed using as a template a full length cDNA of the rat-derived PPO obtained in Example 2, and using as a primer an oligonucleotide having the nucleotide sequence shown in SEQ ID: No. 7 and that having the nucleotide sequence shown in SEQ ID: No. 8 to amplify the about 1.5 kbp DNA fragment encoding the rat PPO. The polymerase chain reaction is performed by adding 10 pmol of an oligonucleotide having the nucleotide sequence shown in SEQ ID: No. 7, 10 pmol of an oligonucleotide having the nucleotide sequence shown in SEQ ID: No. 8, 0.5 µl of Advantage KlenTaq Polymerase Mix (manufactured by Clontech), 2.5 µl of 10×KlenTaq PCR reaction buffer (manufactured by Clontech), each 5 nmol of four kinds of nucleotides (dATP, dCTP, dGTP, dTTP: manufactured by Clontech), and 10 ng of the full length of cDNA of the rat-derived PPO obtained in Example 2 in a 0.2 ml volume of a polymerase chain reaction tube to total amount of 25 µl. Each step in the polymerase chain reaction is performed under the following conditions: After the first cycle comprising a denaturing step holding a temperature at 94° C. for 1 minute, and an annealing step and extension step with a DNA polymerase holding a temperature at 65° C. for 4 minutes is performed once, the second cycle comprising a denaturing step holding a temperature at 94° C. for 30 seconds, and an annealing step and extension step with a DNA polymerase holding a temperature at 65° C. for 4 minutes is performed 15 times. After completion of the polymerase chain reaction, the DNA fragment amplified in the polymerase chain reation is purified by filtering the reaction solution with a spin column (MicroSpin S-400HR manufactured by Pharmacia Biotech). After the end of this DNA fragment is made blunt with a DNA blunting kit (manufactured by TAKARA SHUZO CO., LTD), a phosphate group is added to the 5' end with T4 polynucleotide kinase (manufactured by TAKARA SHUZO CO., LTD). times. After completion of the polymerase chain reaction, the DNA fragment amplified in the polymerase chain reaction is purified by filtering the reaction solution with MicroSpin S-400HR (manufactured by Pharmacia Biotech). After the end of this DNA fragment is made blunt with a DNA blunting kit (manufactured by TAKARA SHUZO CO., LTD), a phosphate group is added to the 5'end with T4 polynucleotide kinase (manufactured by TAKARA SHUZO CO., LTD).

On the other hand, after the GUS expression vector pBI221 derived from pUC19 (manufactured by Clontech) is cut with restriction enzymes SmaI and SacI (both manufactured by TAKARA SHUZO CO., LTD) to recover the 2.8 kbp DNA fragment from which the GUS structural gene has been removed and its end is made blunt using a DNA blunting kit (manufactured by TAKARA SHUZO CO., LTD), the DNA fragment is dephosphorylated with bacterial alkaline phosphatase (manufactured by TAKARA SHUZO CO., LTD).

The aforementioned two DNA fragments are taken in a microtube and ligated using a DNA ligation kit (manufactured by TAKARA SHUZO CO., LTD). A competent cell of *Escherichia coli* strain HB101 (manufactured by TAKARA SHUZO CO., LTD) is transformed with the resultant reaction solution to select a strain which has become ampicillin-resistant. Further, a plasmid in which a coding region for the rat-derived PPO is inserted in a forward direction relative to the cauliflower mosaic virus-derived 35S promoter and the nopaline synthase-derived terminator is selected from plasmids contained in the selected strain, to obtain a rat PPO gene expression vector for directly introducing into a plant.

Example 13
(Construction of a PPO Gene Expression Vector for Indirect Introduction)

In order to express a rat-derived PPO gene to in a plant cell, a PPO gene expression vector for indirect introduction into a plant is constructed.

An oligonucleotide having the nucleotide sequence shown by SEQ ID: No.7 and an oligonucleotide having the nucleotide sequence shown by SEQ ID: No.8 are prepared. The oligonucleotides are synthesized using a DNA synthesizer (PE Applied Systems: Model 394 DNA/RNA Synthesizer), using a solvent for synthesis a solvent for Model 394 DNA/RNA Synthesizer (PE Applied Systems) and using as a reagent for DNA synthesis phosphoamidite reagents corresponding to adenine, cytosine, guanine and thymine (PE Applied Systems). After the synthesized oligonucleotides are purified with an oligonucleotide purifying cartridge (PE Applied Systems: OPC cartridge), they are dried under reduced pressure to prepare the oligonucleotides.

A polymerase chain reaction is performed using as a template the full length cDNA for the rat-derived PPO obtained in Example 2, and using an oligonucleotide having the nucleotide sequence shown in SEQ ID: No. 7 and that having the base sequence shown in SEQ ID: No. 8 to amplify the about 1.5 kbp DNA fragment encoding the rat-derived PPO. The polymerase chain reaction is performed by adding 10 pmol of an oligonucleotide having the nucleotide sequence shown by SEQ ID: No. 7, 10 pmol of an oligonucleotide having the nucleotide sequence shown by SEQ ID: No. 8, 0.5 µl of Advantage KlenTaq Polymerase Mix (manufactured by Clontech), 2.5 µl 10×KlenTaq PCR reaction buffer (manufactured by Clontech),each 5 n mol of four kinds of nucleotides (dATP, dCTP, dGTP, dTTP, manufactured by Clontech), and 10 ng of a DNA containing the full length cDNA for the rat-derived PPO obtained in Example 2 to 0.2 µl volume of a polymerase chain reaction tube to total volume of 25 µ. Each step of the polymerase chain reaction is performed as follows: After the first cycle comprising a denaturing step holding a temperature at 94° C. for 1 minute, and an annealing step and an extension step with a DNA polymerase holding a temperature at 65° C. for 4 minutes is performed once, the second step comprising a denaturing step holding a temperature at 94° C. for 30 seconds, an annealing step and an extension step with a DNA polymerase holding a temperature at 65° C. for 4 minutes is performed 15 times. After completion of the polymerase chain reaction, the DNA fragment amplified by polymerase chain reaction is purified by filtering the reaction solution with MicroSpin S-400HR (manufactured by Pharmacia Biotech). After the end of this DNA fragment is made blunt with a DNA blunting kit (manufactured by TAKARA SHUZO CO., LTD), a phosphate group is added to the 5'end with the T4 polynucleotide kinase (manufactured by TAKARA SHUZO CO., LTD).

On the other hand, after the pBIN19-derived GUS expressing binary vector pBI121 (manufactured by Clontech) is cut with restriction enzymes SmaI and SacI (both manufactured by TAKARA SHUZO CO., LTD) to recover the DNA fragment from which the GUS structural gene has been removed and its end is made blunt using a DNA blunting kit (manufactured by TAKARA SHUZO CO., LTD), it is dephosphorylated with a bacterial alkaline phosphatase (manufactured by TAKARA SHUZO CO., LTD).

The aforementioned two DNA fragments are taken in a microtube and ligated using a DNA ligation kit (manufactured by TAKARA SHUZO CO., LTD). A competent cell of *Escherichia coli* strain HB101 (manufactured by TAKARA SHUZO CO., LTD) is transformed with the resultant reaction solution to select a strain which has become kanamycin-resistant. Further, a plasmid in which a coding region for a rat PPO is inserted in a forward direction relative to the cauliflower mosaic virus-derived 35S promoter and the nopaline synthase-derived terminator from plasmids contained in the selected strain, to obtain the rat PPO gene expression vector for indirect introduction into a plant.

Example 14
(Construction of a Vector for Expressing a *Chlamydomonas reinhardtii* PPO Gene)

In order to express a *Chlamydomonas reinhardtii*-derived PPO in a plant cell, a PPO gene expression vector for direct introduction into a plant is constructed.

The pCR2.1 plasmid harboring the amplified fragment of the cDNA for the *Chlamydomonas reinhardtii*-derived PPO gene obtained in Example 9 is digested with restriction enzymes NotI and SpeI (both manufactured by TAKARA SHUZO CO., LTD) to obtain the about 2 kbp *Chlamydomonas reinhardtii*-derived PPO gene cDNA fragment having cohesive ends for NotI and SpeI at its end. On the other hand, pBluescriptII KS+ (manufactured by Stratagene) is cut with restriction enzymes NotI and SpeI (both manufactured by TAKARA SHUZO CO., LTD) and the 5'end is dephosphorylated with calf intestine alkaline phosphatase (manufactured by TAKARA SHUZO CO., LTD). The two DNA fragments are taken in a microtube and ligated using a DNA ligation kit (manufactured by TAKARA SHUZO CO., LTD). A competent cell of Escherichia coli strain HB101 (manufactured by TAKARA SHUZO CO., LTD) is transformed with the resultant reaction solution to select a strain which has become ampicillin-resistant. Further, a plasmid contained in the selected strain is selected to obtain a clone in which the *Chlamydomonas reinhardtii*-derived PPO gene cDNA is inserted into the plasmid pBluescriptII KS+.

The resultant plasmid is digested with restriction enzymes BamHI and SacI (both manufactured by TAKARA SHUZO CO., LTD) to obtain the about 2 kbp *Chlamydomonas reinhardtii*-derived PPO gene cDNA fragment having cohesive ends for BamHI and SacI at its ends. On the other hand, pBI221 and pBI121 (both manufactured by Clontech) are cut with restriction enzymes BamHI and SacI (both manufactured by TAKARA SHUZO CO., LTD), respectively, to obtain a vector fragment from which a β-glucuronidase gene has been removed and the 5'end is dephosphorylated with the calf intestine alkaline phosphatase (manufactured by TAKARA SHUZO CO., LTD). The *Chlamydomonas reinhardtii*-derived PPO gene cDNA fragment and the two DNA fragments of the vector fragment of pBI221 or pBI121 are taken in a microtube and ligated using a DNA ligation kit (manufactured by TAKARA SHUZO CO., LTD). A competent cell of *Escherichia coli* strain HB101 (manufactured by TAKARA SHUZO CO., LTD) is transformed with the resultant reaction solution and a strain which has become ampicillin-resistant, in the case of ligation with the pBI221 vector fragment and, a plasmid which has become kanamycin-resistant, in the case of ligation with pBI121 vector fragment are selected. Further, a plasmid contained in the selected strain is select to obtain a plasmid for direct introduction in which the *Chlamydomonas reinhardtii*-derived PPO gene cDNA fragment is inserted into the pBI221 vector fragment or a plasmid for indirect introduction in which the *Chlamydomonas reinhardtii*-derived PPO gene cDNA fragment is inserted into the pBI121 vector fragment.

Example 15
(Production of a Transformed Plant in which a Rat or *Chlamydomonas reinhardtii*-Derived PPO Expression Vector is Introduced)

The rat PPO gene expression vector for indirect introduction or the *Chlamydomonas reinhardtii* PPO gene expression vector for indirect induction obtained in Example 13 or Example 14 is transferred into *Agrobacterium tumefaciens* LBA4404 by a binary vector method (manufactured by Clontech: GUS Gene Fusion Ststem). A sterile-cultured tobacco leaf is infected with this bacterial strain according to Plane Gene Manipulation Manual (author: Uchimiya, Kodansha Scientific, 1990) to obtain a transformed tobacco. Similarly, a sterile-cultured carrot seedling petiole is infected therewith according to a method described in N. Pawlicki et al., (1992) Plant Cell, Tissue and Organ Culture, vol.31, pp.129 to 139 to obtain a transformed carrot.

Similarly, a sterile-cultured pea seedling epicotyl or cotyledon is infected therewith according to a method described in J. Puonti-Kaerlas et al., (1990) Theoretical and Applied Genetics, vol.80, pp.246 to 252 to obtain a transformed pea.

Further, the rat PPO gene expression vector for direct introduction or *Chlamydomonas reinhardtii* PPO gene expression vector for direct introduction obtained in Example 12 or Example 15 is introduced into soybean adventitious embryo with a particle gun according to a method described in JP-A-3-291501 (laid-opened) to obtain a transformed soybean. Similarly, it is introduced into a sterile-cultured rice immature scutellum with a particle gun according to a method described in Ikushugakkaishi, vol.44, suppl.No.1, pp.66, (1994)(author: Shimada, et al.) to obtain a transformed rice. Similarly, it is introduced into a sterile-cultured wheat immature scutellum with a particle gun according to the conventional method described in Ikushugakkaishi, vol.44, suppl. No.1, pp.57 (1995) (author: Takumi, et al.) to obtain a transformed wheat. Similarly, it is introduced into a sterile-cultured barley immature scutellum with a particle gun according to a method described in Ikushugakkaishi, vol.44, suppl. No.1, pp.67 (1995)(author: Hagio, et al.) to obtain a transformed barley. Similarly, it is introduced into a corn adventitious embryo with a particle gun according to a method described in M. E. Fromm et al., (1990) BIO/TECHNOLOGY, vol.8, pp.833 to 839 to obtain a transformed corn.

The present invention makes it possible to provide a method for evaluating the ability of a compound to inhibit the PPO activity with simplicity.

Brief Explanation of the Sequence

1. SEQ ID: No.1

Shows the amino acid sequence of a mitochondrial-type PPO encoded in a cDNA for a rat-derived PPO gene.

2. SEQ ID: No.2

Shows the nucleotide sequence of a cDNA clone for a rat-derived PPO gene.

3. SEQ ID: No.3

Shows the nucleotide sequence of an oligonucleotide used for amplifying a DNA fragment containing a partial nucleotide sequence of a rat-derived PPO gene.

4. SEQ ID: No.4

Shows the nucleotide sequence of an oligonucleotide used for amplifying a DNA fragment containing a partial nucleotide sequence of a rat-derived PPO gene.

5. SEQ ID: No. 5

Shows the nucleotide sequence of a primer used for constructing a vector expressing a rat-derived PPO gene in *Escherichia coli*.

6. SEQ ID: No. 6

Shows the nucleotide sequence of a primer used for constructing a vector expressing a rat-derived PPO gene in *Escherichia coli*.

7. SEQ ID: No. 7

Shows the nucleotide sequence of a primer used for constructing a rat-derived PPO gene expression vector for direct introduction and a rat-derived PPO expression vector for indirect introduction.

8. SEQ ID: No.8

Shows the nucleotide sequence of a primer used for constructing a rat-derived PPO gene expression vector for direct introduction and a rat-derived PPO expression vector for indirect introduction.

9. SEQ ID: No. 9

Shows the amino acid sequence of PPO encoded in a cDNA for *Chlamydomonas reinhardtii*-derived PPO gene.

10. SEQ ID: No.10

Shows the nucleotide sequence of a cDNA clone for *Chlamydomonas reinhardtii*-derived PPO gene.

11. SEQ ID: No.11

Shows the nucleotide sequence of an oligonucleotide used for amplifying a DNA fragment containing a *Chlamydomonas reinhardtii*-derived PPO gene.

12. SEQ ID: No.12

Shows the nucleotide sequence of an oligonucleotide used for amplifying a DNA fragment containing a *Chlamydomonas reinhardtii*-derived PPO gene.

13. SEQ ID: No. 13

Shows the nucleotide sequence of a primer used for constructing a vector expressing a *Chlamydomonas reinhardtii*-derived PPO gene in *Escherichia coli*.

14. SEQ ID: No.14

Shows the nucleotide sequence of a primer used for constructing a vector for expressing a *Chlamydomonas reinhardtii*-derived PPO gene in *Escherichia coli*.

What is claimed is:

1. A method for evaluating the ability of a compound to inhibit protoporphyrinogen oxidase activity, comprising the steps of:
   (1) transforming with a vector a host cell deficient in growing ability based on protoporphyrinogen oxidase activity, said vector comprising a DNA fragment coding for enzyme protoporphyrinogen oxidase which is capable of oxidizing protoporphyrinogen into protoporphyrin and which confers growth ability, wherein said DNA fragment is operably linked to a promoter functional in said host cell;
   (2) culturing said transformant expressing said protoporphyrinogen oxidase DNA in a medium containing substantially no protoheme compounds, wherein in a first comparative system there is a presence of a test compound to measure a growth rate of the transformant and in a second comparative system there is an absence of said test compound; and
   (3) determining the ability of the test compound to inhibit the protoporphyrinogen oxidase activity by comparing the growth rates of the first comparative system to the second comparative system, wherein an inhibition of the growth rate is indicative of an inhibition of protoporphyrinogen oxidase activity by said test compound.

2. A method for evaluating the ability of a compound to inhibit protoporphyrinogen oxidase activity, comprising the steps of:
   (1) transforming with a vector a host cell deficient in growing ability based on protoporphyrinogen oxidase activity, said vector comprising a DNA fragment coding for enzyme protoporphyrinogen oxidase which is capable of oxidizing protoporphyrinogen into protoporphyrin and which confers growth ability, wherein said DNA fragment is operably linked to a promoter functional in said host cell, and a terminator functional in the host cell;
   (2) culturing said transformant expressing said protoporphyrinogen oxidase DNA in a medium containing substantially no protoheme compounds, wherein in a first comparative system there is a presence of a test compound to measure a growth rate of the transformant and in a second comparative system there is an absence of said test compound; and
   (3) determining the ability of the test compound to inhibit the protoporphyrinogen oxidase activity by comparing the growth rates of the first comparative system to the second comparative system, wherein an inhibition of the growth rate is indicative of an inhibition of protoporphyrinogen oxidase activity by said test compound.

3. A method for evaluating the ability of a compound to inhibit protoporphyrinogen oxidase activity, comprising the steps of:
   (1) transforming with a vector a host cell deficient in growing ability based on protoporphyrinogen oxidase activity, said vector comprising a DNA fragment coding for enzyme protoporphyrinogen oxidase which is capable of oxidizing protoporphyrinogen into protoporphyrin and which confers growth ability, wherein said DNA fragment is operably linked to a promoter functional in said host cell, wherein said promoter is inducible, and a second vector comprising a second DNA fragment which is a DNA capable of inducing the promoter of the first DNA fragment, and a promoter, wherein said promoter is not induced by the second DNA fragment but is functional in the host cell, are operatively linked;

(2) culturing said transformant expressing said protoporphyrinogen oxidase DNA in a medium containing substantially no protoheme compounds, wherein in a first comparative system there is a presence of a test compound to measure a growth rate of the transformant and in a second comparative system there is an absence of said test compound; and (3) determining the ability of the test compound to inhibit the protoporphyrinogen oxidase activity by comparing the growth rates of the first comparative system to the second comparative system, wherein an inhibition of the growth rate is indicative of an inhibition of protoporphyrinogen oxidase activity by said test compound.

4. A method for evaluating the ability of a compound to inhibit protoporphyrinogen oxidase activity, comprising the steps of:

(1) transforming with a vector a host cell deficient in growing ability based on protoporphyrinogen oxidase activity, said vector comprising a DNA fragment coding for enzyme protoporphyrinogen oxidase which is capable of oxidizing protoporphyrinogen into protoporphyrin and which confers growth ability, wherein said DNA fragment is operably linked to a promoter functional in said host cell, and a terminator functional in the host cell, wherein said promoter is inducible, and a second vector comprising a second DNA fragment in which a DNA being capable of inducing the promoter of the first DNA fragment, a promoter, wherein said promoter is not induced by the DNA fragment but is functional in the host cell, and a terminator functionable in the host cell are operatively linked;

(2) culturing said transformant expressing said protoporphyrinogen oxidase DNA in a medium containing substantially no protoheme compounds, wherein in a first comparative system there is a presence of a test compound to measure a growth rate of the transformant and in a second comparative system there is an absence of said test compound; and (3) determining the ability of the test compound to inhibit the protoporphyrinogen oxidase activity by comparing the growth rates of the first comparative system to the second comparative system, wherein an inhibition of the growth rate is indicative of an inhibition of protoporphyrinogen oxidase activity by said test compound.

5. The method according to claim 1 or 3, wherein the host cell is an *E. coli* or a yeast cell.

6. The method of claim 1, 2, 3, or 4, wherein said DNA fragment coding for enzyme protoporphyrinogen oxidase comprises SEQ ID NO:2 or SEQ ID NO:10.

* * * * *

US006472164C1

(12) EX PARTE REEXAMINATION CERTIFICATE (6593rd)
United States Patent
Shimokawatoko et al.

(10) Number: US 6,472,164 C1
(45) Certificate Issued: Dec. 30, 2008

(54) METHOD FOR EVALUATING THE ABILITY OF A COMPOUND TO INHIBIT THE PROTOPORPHYRINOGEN OXIDASE ACTIVITY

(75) Inventors: Yasutaka Shimokawatoko, Kobe (JP); Shoichi Nishio, Toyonaka (JP)

(73) Assignee: Sumitomo Chemical Company, Ltd., Osaka (JP)

Reexamination Request:
No. 90/008,185, Aug. 23, 2006

Reexamination Certificate for:
Patent No.: 6,472,164
Issued: Oct. 29, 2002
Appl. No.: 09/289,180
Filed: Apr. 9, 1999

(30) Foreign Application Priority Data

Apr. 10, 1998 (JP) ............................................. 10-099619

(51) Int. Cl.
*C12Q 1/68* (2006.01)
*C12N 9/02* (2006.01)

(52) U.S. Cl. ........................ 435/25; 435/189; 435/252.3; 435/320.1; 435/325; 536/23.2

(58) Field of Classification Search ...................... None
See application file for complete search history.

(56) References Cited

PUBLICATIONS

Vieira et al., "The pUC plasmids, an M13mp7—derived system for insertion mutagenesis and sequencing with synthetic universal primers," Gene, vol. 19, (1982), pp. 259–268.*
Narita et al., "Molecular cloning and characteristics of a cDNA that encodes protoporphyrinogen oxidase of *Arabidopsis thaliana*," Gene, vol. 182, (1996), pp. 169–175.

* cited by examiner

*Primary Examiner*—Sharon Turner

(57) ABSTRACT

The present invention provides a method for evaluating the ability of a compound to inhibit protoporphyrinogen oxidase activity with a host cell deficient in protoporphyrinogen oxidase production which has been transformed with a vector comprising a DNA fragment encoding a protoporphyrinogen oxidase. Transformed cells are grown in protoheme-free medium in the presence and absence of test compounds and growth rates measured under these condition are compared to determine if inhibition has occurred.

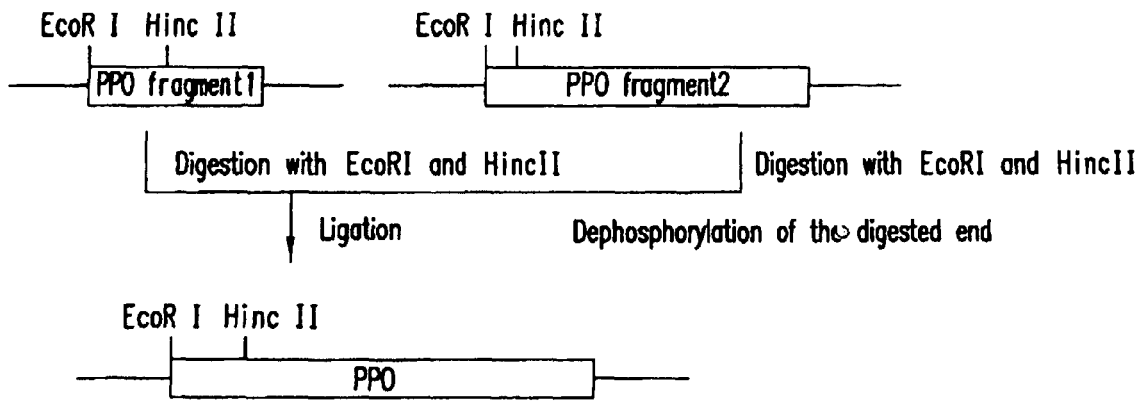

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3–4 is confirmed.

Claims 1–2 are determined to be patentable as amended.

Claims 5–6, dependent on an amended claim, are determined to be patentable.

New claims 7–8 are added and determined to be patentable.

1. A method for evaluating the ability of a compound to inhibit protoporphyrinogen oxidase activity, comprising the steps of:
   (1) transforming with a vector a host cell deficient in growing ability based on protoporphyrinogen oxidase activity, said vector comprising a DNA fragment coding for enzyme protoporphyrinogen oxidase which is capable of oxidizing protoporphyrinogen into protoporphyrin and which confers growth ability, wherein said DNA fragment is operably linked to a promoter functional in said host cell, *wherein said promoter is controllable, and a second vector comprising a second DNA fragment which is a DNA capable of controlling the transcriptional activity of the promoter of the first DNA fragment, and a promoter, wherein said promoter is not controlled by the second DNA fragment but is functional in the host cell, are operatively linked*;
   (2) culturing said transformant expressing said protoporphyrinogen oxidase DNA in a medium containing substantially no protoheme compounds, wherein in a first comparative system there is a presence of a test compound to measure a growth rate of the transformant and in a second comparative system there is an absence of said test compound; and
   (3) determining the ability of the test compound to inhibit the protoporphyrinogen oxidase activity by comparing the growth rates of the first comparative system to the second comparative system, wherein an inhibition of the growth rate is indicative of an inhibition of protoporphyrinogen oxidase activity by said test compound.

2. A method for evaluating the ability of a compound to inhibit protoporphyrinogen oxidase activity, comprising the steps of:
   (1) transforming with a vector a host cell deficient in growing ability based on protoporphyrinogen oxidase activity, said vector comprising a DNA fragment coding for enzyme protoporphyrinogen oxidase which is capable of oxidizing protoporphyrinogen into protoporphyrin and which confers growth ability, wherein said DNA fragment is operably linked to a promoter functional in said host cell, and a terminator functional in the host cell, *wherein said promoter is controllable, and a second vector comprising a second DNA fragment which is a DNA capable of controlling the transcriptional activity of the promoter of the first DNA fragment, and a promoter, wherein said promoter is not controlled by the second DNA fragment but is functional in the host cell, are operatively linked*;
   (2) culturing said transformant expressing said protoporphyrinogen oxidase DNA in a medium containing substantially no protoheme compounds, wherein in a first comparative system there is a presence of a test compound to measure a growth rate of the transformant and in a second comparative system there is an absence of said test compound; and
   (3) determining the ability of the test compound to inhibit the protoporphyrinogen oxidase activity by comparing the growth rates of the first comparative system to the second comparative system, wherein an inhibition of the growth rate is indicative of an inhibition of protoporphyrinogen oxidase activity by said test compound.

7. *The method according to claim 1 or 2, wherein the second DNA fragment is a DNA capable of inhibiting the transcriptional activity of the promoter of the first DNA fragment.*

8. *The method according to claim 1 or 2, wherein the second DNA fragment is a DNA capable of promoting the transcriptional activity of the promoter of the first DNA fragment.*

* * * * *